(12) United States Patent
Davidson et al.

(10) Patent No.: US 7,771,462 B1
(45) Date of Patent: Aug. 10, 2010

(54) CATHETER WITH SIDE SHEATH AND METHODS

(75) Inventors: Charles J. Davidson, Winnetka, IL (US); Gil M. Vardi, Town and Country, MO (US); Eric Williams, Fairfield, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 09/663,111

(22) Filed: Sep. 15, 2000

Related U.S. Application Data

(63) Continuation of application No. 09/614,472, filed on Jul. 11, 2000, now abandoned, which is a continuation of application No. 09/325,996, filed on Jun. 4, 1999, now abandoned, application No. 09/663,111, which is a continuation-in-part of application No. 09/455,299, filed on Dec. 6, 1999, now Pat. No. 6,692,483.

(51) Int. Cl.
*A61F 2/06* (2006.01)

(52) U.S. Cl. .................... 623/1.11; 623/1.23; 623/1.34; 623/1.35

(58) Field of Classification Search .............. 604/98.01, 604/103.04, 101.04, 264, 523, 529; 606/108, 606/153, 195; 623/1.11, 1.23, 1.34, 1.35
See application file for complete search history.

(56) References Cited

U.S. PATENT DOCUMENTS

| 1,596,754 | A | | 8/1926 | Mochelle |
| 3,657,744 | A | | 4/1972 | Ersek |
| 3,872,893 | A | | 3/1975 | Roberts |
| 4,140,126 | A | | 2/1979 | Choudhury |
| 4,309,994 | A | | 1/1982 | Grunwald |
| 4,385,631 | A | * | 5/1983 | Uthmann ............. 604/284 |
| 4,410,476 | A | | 10/1983 | Redding et al. |
| 4,413,989 | A | | 11/1983 | Schjeldahl |

(Continued)

FOREIGN PATENT DOCUMENTS

CA 2318314 7/1999

(Continued)

OTHER PUBLICATIONS

SCIMED Life Systems, Inc.—TRIO™ 14 PTCA Catheter, Re-engineering Over-the-Wire-Balloon Technology, Company Brochure, 1994.

(Continued)

*Primary Examiner*—Paul Prebilic
(74) *Attorney, Agent, or Firm*—Crompton, Seager & Tufte, LLC

(57) ABSTRACT

A catheter system comprises a catheter having a catheter body with a distal end, a proximal end, a main vessel guidewire lumen for receiving a main vessel guidewire and a balloon disposing at the distal end of the catheter body. The catheter further includes a side member that is disposed adjacent to the catheter body. The side member has a distal end, a proximal end, and a branch vessel guidewire lumen for receiving a branch vessel guidewire. A stent having a side hole is disposed over the balloon, and a distal portion of the side member is disposed beneath at least a portion of the stent while being adjacent to and movable with respect to the balloon.

42 Claims, 24 Drawing Sheets

U.S. PATENT DOCUMENTS

| | | | |
|---|---|---|---|
| 4,421,810 A | 12/1983 | Rasmussen | |
| 4,453,545 A | 6/1984 | Inoue | |
| 4,503,569 A | 3/1985 | Dotter | |
| 4,552,554 A | 11/1985 | Gould et al. | |
| 4,681,570 A | 7/1987 | Dalton | |
| 4,689,174 A | 8/1987 | Lupke | |
| 4,731,055 A | 3/1988 | Melinyshyn et al. | |
| 4,733,665 A | 3/1988 | Palmaz | |
| 4,739,762 A | 4/1988 | Palmaz | |
| 4,759,748 A | 7/1988 | Reed | 604/95 |
| 4,762,128 A | 8/1988 | Rosenbluth | |
| 4,769,029 A | 9/1988 | Patel | |
| 4,819,664 A | 4/1989 | Nazari | |
| 4,872,874 A | 10/1989 | Taheri | |
| 4,878,495 A | 11/1989 | Grayzel | |
| 4,896,670 A | 1/1990 | Crittenden | |
| 4,900,314 A | 2/1990 | Quackenbush | |
| 4,906,244 A | 3/1990 | Pinchuk et al. | |
| 4,909,258 A | 3/1990 | Kuntz et al. | |
| 4,946,464 A | 8/1990 | Pevsner | |
| 4,957,501 A | 9/1990 | Lahille et al. | |
| 4,957,508 A | 9/1990 | Kaneko et al. | |
| 4,964,850 A | 10/1990 | Bouton et al. | |
| 4,983,167 A | 1/1991 | Sahota | |
| 4,994,071 A | 2/1991 | MacGregor | |
| 5,042,976 A | 8/1991 | Ishitsu et al. | |
| 5,054,501 A | 10/1991 | Chuttani et al. | |
| 5,059,170 A * | 10/1991 | Cameron | 604/43 |
| 5,059,177 A | 10/1991 | Towne et al. | |
| 5,061,240 A | 10/1991 | Cherian | |
| 5,064,435 A | 11/1991 | Porter | |
| 5,085,664 A | 2/1992 | Bozzo | |
| 5,102,403 A | 4/1992 | Alt | |
| 5,102,417 A | 4/1992 | Palmaz | |
| 5,104,404 A | 4/1992 | Wolff | |
| 5,117,831 A | 6/1992 | Jang | |
| 5,122,125 A | 6/1992 | Deuss | |
| 5,135,536 A | 8/1992 | Hillstead | |
| 5,147,317 A | 9/1992 | Shank et al. | |
| 5,159,920 A | 11/1992 | Condon et al. | |
| 5,176,617 A | 1/1993 | Fischell et al. | |
| 5,192,297 A | 3/1993 | Hull | |
| 5,195,984 A | 3/1993 | Schatz | |
| 5,211,683 A | 5/1993 | Maginot | |
| 5,217,440 A | 6/1993 | Frassica | |
| 5,222,971 A | 6/1993 | Willard et al. | |
| 5,226,913 A | 7/1993 | Pinchuk | |
| 5,234,457 A | 8/1993 | Andersen | |
| 5,236,446 A | 8/1993 | Dumon | |
| 5,244,619 A | 9/1993 | Burnham | |
| 5,254,619 A | 10/1993 | Ando | |
| 5,257,974 A | 11/1993 | Cox | |
| 5,263,932 A | 11/1993 | Jang | |
| 5,282,472 A | 2/1994 | Companion et al. | |
| 5,304,220 A | 4/1994 | Maginot | |
| 5,320,605 A | 6/1994 | Sahota | |
| 5,324,257 A | 6/1994 | Osborne et al. | |
| 5,337,733 A | 8/1994 | Bauerfeind et al. | |
| 5,338,300 A | 8/1994 | Cox | |
| 5,342,295 A | 8/1994 | Imran | |
| 5,342,297 A | 8/1994 | Jang | |
| 5,342,387 A | 8/1994 | Summers | |
| 5,350,395 A * | 9/1994 | Yock | 606/194 |
| 5,383,892 A | 1/1995 | Ansel | |
| 5,387,235 A | 2/1995 | Chuter | |
| 5,395,332 A | 3/1995 | Ressemann et al. | |
| 5,395,334 A | 3/1995 | Keith et al. | |
| 5,404,887 A | 4/1995 | Prather | |
| 5,409,458 A | 4/1995 | Khairkhahan et al. | |
| 5,413,581 A | 5/1995 | Goy | |
| 5,413,586 A | 5/1995 | Dibie et al. | |
| 5,417,208 A | 5/1995 | Winkler | |
| 5,425,765 A | 6/1995 | Tiefenbrun et al. | |
| 5,437,638 A | 8/1995 | Bowman | |
| 5,443,497 A | 8/1995 | Venbrux | |
| 5,445,624 A | 8/1995 | Jiminez | |
| 5,449,373 A | 9/1995 | Pinchasik et al. | |
| 5,449,382 A | 9/1995 | Dayton | |
| 5,456,694 A | 10/1995 | Marin et al. | |
| 5,456,712 A | 10/1995 | Maginot | |
| 5,456,714 A | 10/1995 | Owen | |
| 5,458,605 A | 10/1995 | Klemm | |
| 5,462,530 A | 10/1995 | Jang | |
| 5,476,471 A | 12/1995 | Shifrin et al. | |
| 5,489,271 A | 2/1996 | Andersen | |
| 5,489,295 A | 2/1996 | Piplani et al. | |
| 5,496,292 A | 3/1996 | Burnham | |
| 5,505,702 A | 4/1996 | Arney | |
| 5,507,768 A | 4/1996 | Lau | |
| 5,507,769 A | 4/1996 | Marin et al. | |
| 5,514,154 A | 5/1996 | Lau et al. | |
| 5,514,178 A | 5/1996 | Torchio | |
| 5,522,801 A | 6/1996 | Wang | |
| 5,531,788 A | 7/1996 | Dibie et al. | |
| 5,545,132 A | 8/1996 | Fagan et al. | |
| 5,549,553 A | 8/1996 | Ressemann et al. | |
| 5,549,554 A | 8/1996 | Miraki | |
| 5,562,620 A | 10/1996 | Klein et al. | |
| 5,562,724 A | 10/1996 | Vorwerk et al. | |
| 5,562,725 A | 10/1996 | Schmitt et al. | |
| 5,562,726 A | 10/1996 | Chuter | |
| 5,569,295 A | 10/1996 | Lam | |
| 5,571,087 A | 11/1996 | Ressemann et al. | |
| 5,575,771 A | 11/1996 | Walinsky | |
| 5,575,818 A | 11/1996 | Pinchuk | |
| 5,591,228 A | 1/1997 | Edoga | |
| 5,593,442 A | 1/1997 | Klein | |
| 5,607,444 A | 3/1997 | Lam | |
| 5,609,605 A | 3/1997 | Marshall et al. | |
| 5,609,625 A | 3/1997 | Piplani et al. | |
| 5,609,627 A | 3/1997 | Goicoechea et al. | |
| 5,609,629 A | 3/1997 | Fearnot et al. | |
| 5,613,949 A | 3/1997 | Miraki | |
| 5,613,980 A | 3/1997 | Chauhan | 606/194 |
| 5,613,981 A | 3/1997 | Boyle et al. | |
| 5,617,878 A | 4/1997 | Taheri | |
| 5,626,600 A | 5/1997 | Horzewski et al. | |
| 5,628,788 A | 5/1997 | Pinchuk | |
| 5,632,762 A | 5/1997 | Myler | |
| 5,632,763 A | 5/1997 | Glastra | |
| 5,632,772 A | 5/1997 | Alcime et al. | |
| 5,634,902 A | 6/1997 | Johnson et al. | |
| 5,639,278 A | 6/1997 | Dereume et al. | |
| 5,643,340 A | 7/1997 | Nunokawa | |
| 5,653,743 A | 8/1997 | Martin | |
| 5,662,614 A | 9/1997 | Edoga | |
| 5,669,924 A | 9/1997 | Shaknovich | |
| 5,669,932 A | 9/1997 | Fischell et al. | |
| 5,676,696 A | 10/1997 | Morcade | |
| 5,676,697 A | 10/1997 | McDonald | |
| 5,679,400 A | 10/1997 | Tuch | |
| 5,683,451 A * | 11/1997 | Lenker et al. | 623/1.11 |
| 5,690,642 A | 11/1997 | Osborne et al. | |
| 5,693,084 A | 12/1997 | Chutter | |
| 5,693,086 A | 12/1997 | Goicoechea et al. | |
| 5,693,088 A | 12/1997 | Lazarus | |
| 5,697,971 A | 12/1997 | Fischell et al. | |
| 5,707,354 A | 1/1998 | Salmon | |
| 5,709,713 A | 1/1998 | Evan et al. | |
| 5,716,365 A | 2/1998 | Goicoechea et al. | |
| 5,718,683 A | 2/1998 | Ressemann et al. | |
| 5,718,724 A | 2/1998 | Goicoechea et al. | |
| 5,720,735 A | 2/1998 | Dorros | |
| 5,723,004 A | 3/1998 | Dereume et al. | |

| | | | | | | |
|---|---|---|---|---|---|---|
| 5,724,977 A | 3/1998 | Yock et al. | | 6,048,361 A | 4/2000 | Von Oepen |
| 5,728,158 A | 3/1998 | Lau et al. | | 6,056,775 A | 5/2000 | Borghi et al. |
| 5,733,303 A | 3/1998 | Israel et al. | | 6,059,823 A | 5/2000 | Holman et al. |
| 5,735,893 A | 4/1998 | Lau et al. | | 6,059,824 A | 5/2000 | Taheri |
| 5,746,766 A | 5/1998 | Edoga | | 6,066,168 A | 5/2000 | Lau et al. |
| 5,749,825 A | 5/1998 | Fischell et al. | | 6,068,655 A | 5/2000 | Seguin et al. |
| 5,749,848 A | 5/1998 | Jang et al. | | 6,071,285 A | 6/2000 | Lashinski et al. |
| 5,755,734 A | 5/1998 | Richter et al. | | 6,086,611 A | 7/2000 | Duffy et al. |
| 5,755,735 A | 5/1998 | Richter et al. | | 6,090,127 A | 7/2000 | Globerman |
| 5,755,770 A | 5/1998 | Ravenscroft | | 6,090,128 A | 7/2000 | Douglas |
| 5,755,771 A | 5/1998 | Penn et al. | | 6,096,073 A | 8/2000 | Webster et al. .............. 623/1.16 |
| 5,755,778 A | 5/1998 | Kleshinski | | 6,099,497 A | 8/2000 | Adams et al. ............. 604/96.01 |
| 5,762,631 A | 6/1998 | Klein | | 6,102,938 A * | 8/2000 | Evans et al. ................. 623/1.35 |
| 5,776,101 A | 7/1998 | Goy | | 6,117,117 A | 9/2000 | Mauch |
| 5,776,161 A | 7/1998 | Globerman | | 6,117,156 A | 9/2000 | Richter et al. |
| 5,776,180 A | 7/1998 | Goicoechea et al. | | 6,126,685 A | 10/2000 | Lenker et al. |
| 5,782,906 A | 7/1998 | Marshall et al. | | 6,129,738 A | 10/2000 | Lashinski et al. |
| 5,800,450 A | 9/1998 | Lary et al. | | 6,129,754 A | 10/2000 | Kanesaka et al. |
| 5,800,508 A | 9/1998 | Goicoechea et al. | | 6,142,973 A | 11/2000 | Carleton et al. |
| 5,814,061 A | 9/1998 | Osborne et al. | | 6,152,945 A | 11/2000 | Bachinski et al. |
| 5,817,126 A | 10/1998 | Imran | | 6,165,195 A | 12/2000 | Wilson et al. |
| 5,824,008 A | 10/1998 | Bolduc et al. | | 6,165,197 A | 12/2000 | Yock |
| 5,824,036 A | 10/1998 | Lauterjung | | 6,165,214 A | 12/2000 | Lazarus |
| 5,824,039 A * | 10/1998 | Piplani et al. ............... 623/1.11 | | 6,179,867 B1 | 1/2001 | Cox |
| 5,824,040 A | 10/1998 | Cox et al. | | 6,183,506 B1 | 2/2001 | Penn et al. |
| 5,824,041 A | 10/1998 | Lenker et al. | | 6,183,509 B1 | 2/2001 | Dibie |
| 5,824,042 A * | 10/1998 | Lombardi et al. .......... 623/1.13 | | 6,190,353 B1 | 2/2001 | Makower et al. |
| 5,824,044 A | 10/1998 | Quiachon et al. | | 6,190,403 B1 | 2/2001 | Fischell et al. |
| 5,827,320 A | 10/1998 | Richter et al. | | 6,193,746 B1 | 2/2001 | Strecker |
| 5,833,650 A | 11/1998 | Imran | | 6,203,568 B1 | 3/2001 | Lombardi et al. |
| 5,836,966 A | 11/1998 | St. Germain | | 6,203,569 B1 | 3/2001 | Wijay |
| 5,837,008 A | 11/1998 | Berg et al. | | 6,210,380 B1 | 4/2001 | Mauch |
| 5,843,031 A | 12/1998 | Hermann et al. ............... 604/95 | | 6,210,429 B1 | 4/2001 | Vardi |
| 5,843,160 A | 12/1998 | Rhodes | | 6,217,527 B1 | 4/2001 | Selmon et al. |
| 5,843,164 A | 12/1998 | Frantzen et al. | | 6,217,608 B1 | 4/2001 | Penn et al. |
| 5,846,204 A | 12/1998 | Solomon | | 6,221,080 B1 | 4/2001 | Power |
| 5,851,210 A | 12/1998 | Torossian | | 6,221,090 B1 | 4/2001 | Wilson |
| 5,851,464 A * | 12/1998 | Davila et al. ................. 264/103 | | 6,221,098 B1 | 4/2001 | Wilson et al. |
| 5,855,600 A | 1/1999 | Alt | | 6,231,563 B1 | 5/2001 | White et al. |
| 5,855,601 A | 1/1999 | Bessler et al. | | 6,231,598 B1 | 5/2001 | Berry et al. |
| 5,865,178 A | 2/1999 | Yock | | 6,231,600 B1 | 5/2001 | Zhong |
| 5,868,777 A | 2/1999 | Lam | | 6,235,051 B1 | 5/2001 | Murphy |
| 5,871,536 A | 2/1999 | Lazarus | | 6,241,762 B1 | 6/2001 | Shanley |
| 5,871,537 A | 2/1999 | Holman et al. | | 6,251,133 B1 | 6/2001 | Richter et al. |
| 5,891,133 A | 4/1999 | Murphy-Chutorian | | 6,258,073 B1 | 7/2001 | Mauch |
| 5,897,588 A | 4/1999 | Hull et al. | | 6,258,099 B1 | 7/2001 | Mareiro et al. |
| 5,906,640 A | 5/1999 | Penn et al. | | 6,258,116 B1 | 7/2001 | Hojeibane |
| 5,907,893 A | 6/1999 | Zadno-Azizi et al. | | 6,258,121 B1 | 7/2001 | Yang et al. |
| 5,913,895 A | 6/1999 | Burpee et al. | | 6,261,273 B1 | 7/2001 | Ruiz |
| 5,913,897 A | 6/1999 | Corso, Jr. et al. | | 6,261,305 B1 | 7/2001 | Marotta et al. |
| 5,921,958 A | 7/1999 | Ressemann et al. | | 6,261,319 B1 | 7/2001 | Kveen et al. |
| 5,922,020 A | 7/1999 | Klein et al. | | 6,264,682 B1 | 7/2001 | Wilson et al. |
| 5,928,248 A | 7/1999 | Acker | | 6,273,911 B1 | 8/2001 | Cox et al. |
| 5,938,682 A | 8/1999 | Hojeibane | | 6,273,913 B1 | 8/2001 | Wright et al. |
| 5,938,696 A | 8/1999 | Goicoechea et al. | | 6,287,314 B1 | 9/2001 | Lee et al. |
| 5,948,016 A | 9/1999 | Jang | | 6,290,673 B1 | 9/2001 | Shanley |
| 5,951,599 A | 9/1999 | McCrory | | 6,293,967 B1 | 9/2001 | Shanley |
| 5,961,548 A | 10/1999 | Shmulewitz | | 6,299,634 B1 | 10/2001 | Bergeron |
| 5,967,986 A | 10/1999 | Cimochowski et al. | | 6,302,906 B1 | 10/2001 | Goicoechea et al. |
| 5,972,018 A | 10/1999 | Israel et al. | | 6,309,412 B1 | 10/2001 | Lau et al. |
| 6,007,517 A | 12/1999 | Anderson | | 6,309,414 B1 | 10/2001 | Rolando et al. |
| 6,013,054 A | 1/2000 | Jiun Yan | | 6,312,459 B1 | 11/2001 | Huang et al. |
| 6,013,091 A | 1/2000 | Ley et al. | | 6,325,821 B1 | 12/2001 | Gaschino et al. |
| 6,017,324 A | 1/2000 | Tu et al. | | 6,325,826 B1 | 12/2001 | Vardi et al. |
| 6,017,363 A | 1/2000 | Hojeibane | | 6,334,870 B1 | 1/2002 | Her et al. |
| 6,024,763 A | 2/2000 | Lenker et al. | | 6,346,089 B1 | 2/2002 | Dibie |
| 6,030,414 A | 2/2000 | Taheri | | 6,350,278 B1 | 2/2002 | Lenker et al. |
| 6,033,434 A | 3/2000 | Borghi | | 6,355,060 B1 | 3/2002 | Lenker et al. |
| 6,033,435 A | 3/2000 | Penn et al. | | 6,361,544 B1 | 3/2002 | Wilson et al. |
| 6,036,682 A | 3/2000 | Lange et al. | | 6,361,555 B1 | 3/2002 | Wilson |
| 6,039,749 A | 3/2000 | Marin et al. | | 6,383,215 B1 | 5/2002 | Sass |
| 6,042,597 A | 3/2000 | Kveen et al. | | 6,387,120 B2 | 5/2002 | Wilson et al. |
| 6,045,557 A | 4/2000 | White et al. | | 6,395,018 B1 | 5/2002 | Castaneda |

| | | |
|---|---|---|
| 6,398,792 B1 | 6/2002 | O'Connor |
| 6,398,804 B1 | 6/2002 | Spielberg |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 * | 8/2002 | Richter et al. ............... 623/1.15 |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,572,647 B1 | 6/2003 | Supper et al. |
| 6,576,009 B2 * | 6/2003 | Ryan et al. ................. 623/1.35 |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. |
| 6,596,022 B2 | 7/2003 | Lau et al. |
| 6,599,316 B2 | 7/2003 | Vardi et al. |
| 6,645,241 B1 | 11/2003 | Strecker |
| 6,682,536 B2 * | 1/2004 | Vardi et al. ................. 606/108 |
| 6,689,156 B1 | 2/2004 | Davidson et al. |
| 6,692,483 B2 * | 2/2004 | Vardi et al. ................. 604/529 |
| 6,706,062 B2 | 3/2004 | Vardi et al. |
| 6,843,803 B2 * | 1/2005 | Ryan et al. ................. 623/1.35 |
| 6,884,258 B2 * | 4/2005 | Vardi et al. ................. 623/1.11 |
| 6,896,699 B2 * | 5/2005 | Wilson et al. ............... 623/1.35 |
| 6,955,687 B2 | 10/2005 | Richter et al. |
| 6,955,688 B2 * | 10/2005 | Wilson et al. ............... 623/1.35 |
| 6,962,602 B2 | 11/2005 | Vardi et al. |
| 6,980,174 B2 | 12/2005 | Flasza et al. |
| 7,118,593 B2 | 10/2006 | Davidson et al. |
| 7,220,275 B2 | 5/2007 | Davidson et al. |
| 7,244,853 B2 | 7/2007 | Schreiber et al. |
| 7,387,639 B2 | 6/2008 | Bourang et al. |
| 7,445,610 B2 * | 11/2008 | Adams et al. ............ 604/96.01 |
| 2001/0012927 A1 | 8/2001 | Mauch |
| 2001/0016767 A1 | 8/2001 | Wilson et al. |
| 2001/0016768 A1 | 8/2001 | Wilson et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Dibie |
| 2001/0039488 A1 | 11/2001 | Dibie |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Bockstegers et al. |
| 2002/0035392 A1 | 3/2002 | Wilson |
| 2002/0042650 A1 | 4/2002 | Vardi et al. |
| 2002/0052648 A1 | 5/2002 | McGuckin et al. |
| 2002/0058990 A1 | 5/2002 | Jang |
| 2002/0072790 A1 | 6/2002 | McGuckin et al. |
| 2002/0107564 A1 | 8/2002 | Cox et al. |
| 2002/0111675 A1 * | 8/2002 | Wilson ..................... 623/1.35 |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 | 12/2002 | Callol et al. |
| 2002/0193872 A1 | 12/2002 | Trout et al. |
| 2002/0193873 A1 | 12/2002 | Brucker et al. |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0050688 A1 | 3/2003 | Fischell et al. |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon et al. |
| 2003/0125802 A1 | 7/2003 | Callol et al. |
| 2003/0125971 A1 | 7/2003 | Sequin et al. |
| 2003/0181923 A1 | 9/2003 | Vardi |
| 2004/0015227 A1 | 1/2004 | Vardi et al. |
| 2004/0049259 A1 | 3/2004 | Strecker |
| 2004/0148006 A1 | 7/2004 | Davidson et al. |
| 2005/0015135 A1 * | 1/2005 | Shanley ..................... 623/1.11 |
| 2005/0075722 A1 * | 4/2005 | Chuter ..................... 623/1.35 |
| 2005/0154442 A1 | 7/2005 | Eidenschink et al. |
| 2005/0187602 A1 | 8/2005 | Eidenschink |
| 2005/0245941 A1 | 11/2005 | Vardi et al. |
| 2007/0179591 A1 * | 8/2007 | Baker et al. ................. 623/1.23 |
| 2007/0203562 A1 | 8/2007 | Malewicz et al. |
| 2008/0255581 A1 | 10/2008 | Bourang et al. |

FOREIGN PATENT DOCUMENTS

| | | |
|---|---|---|
| CA | 2403826 | 9/2001 |
| DE | 9014845.2 | 2/1991 |
| DE | 29701758 | 5/1997 |
| DE | 29701758 | 7/1997 |
| DE | 60036233 | 5/2008 |
| EP | 804907 | 11/1977 |
| EP | 551179 | 7/1993 |
| EP | 684022 | 11/1995 |
| EP | 804907 | 5/1997 |
| EP | 876805 | 11/1998 |
| EP | 884028 | 12/1998 |
| EP | 891751 | 1/1999 |
| EP | 0 897 700 A | 2/1999 |
| EP | 897698 | 2/1999 |
| EP | 897700 | 2/1999 |
| EP | 0 904 745 A | 3/1999 |
| EP | 904745 | 3/1999 |
| EP | 1031328 | 8/2000 |
| EP | 1031330 | 8/2000 |
| EP | 1157674 | 11/2001 |
| EP | 646365 | 1/2004 |
| EP | 1182989 | 12/2004 |
| EP | 1512380 | 8/2007 |
| FR | 2675808 | 7/1991 |
| FR | 2678508 | 7/1991 |
| FR | 2678508 | 1/1993 |
| WO | WO 88/06026 | 2/1988 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 95/08965 | 4/1995 |
| WO | WO 95/21592 | 8/1995 |
| WO | WO 96/41592 | 6/1996 |

| | | |
|---|---|---|
| WO | 9629955 | 10/1996 |
| WO | 96/34580 | 11/1996 |
| WO | WO 96/41592 | 12/1996 |
| WO | WO 97/09946 | 3/1997 |
| WO | WO 97/33532 | 3/1997 |
| WO | WO 97/16217 | 5/1997 |
| WO | WO 97/45073 | 5/1997 |
| WO | WO 97/26936 | 7/1997 |
| WO | WO 97/26936 A1 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37633 | 9/1998 |
| WO | WO 98/44871 | 10/1998 |
| WO | WO 98/48733 | 11/1998 |
| WO | WO 98/52497 | 11/1998 |
| WO | 9900835 | 1/1999 |
| WO | WO 99/15103 | 4/1999 |
| WO | WO 99/15103 A | 4/1999 |
| WO | WO 99/17680 | 4/1999 |
| WO | 9935979 | 7/1999 |
| WO | WO 99/34749 | 7/1999 |
| WO | WO 99/36002 | 7/1999 |
| WO | WO 99/36002 A1 * | 7/1999 |
| WO | WO 99/39661 | 8/1999 |
| WO | 9949793 | 10/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |
| WO | 2004026180 | 4/2004 |
| WO | 2006124162 | 11/2006 |

OTHER PUBLICATIONS

Caputo et al., "Stent Jail: A Minimum-Security Prison" The American Journal of Cardiology, (1996) 7:1226-1230.
Fischman et al., "A Randomized Comparison of Coronary-Stent Placement and Balloon Angioplasty in the Treatment of Coronary Artery Disease" The New England Journal of Medicine, (1994) 331(8): 496-501.
Nakamura et al., "Techniques for Palmaz-Schatz Stent Deployment in Lesions with a Large Side Branch" Catheterization & Cardiovascular Diagnosis, (1995) 34:353-361.
Serruys et al., "A Comparison of Balloon-Expandable-Stent Implantation with Balloon Angioplasty in Patients with Coronary Artery Disease" The New England Journal of Medicine, (1994) 331(8): 489-495.
Colombo et al., "Kissing' Stents for Bifucational Coronary Lesion" Catheterization and Cardiovascular Diagnosis, (1993) 30:327-330.
Carrie et al., "T'-Shaped Stent Placement":A Technique for the Treatment of Dissected Bifurcation Lesions Catheterization and Cardiovascular Diagnosis, (1996) 37:311-313.
Katoh et al., "New Double Wire Technique to Stent Ostial Lesions" Catheterization and Cardiovascular Diagnosis, (1997) 40:400-402.
SCIMED Life Systems, Inc.—Trio™ PTCA Catheter, Re-engineering Over-the-Wire Balloon Technology, Company Brochure, © 1994.

Caputo et al., "Stent Jail: A Minimum-Security Prison": The American Journal of Cardiology, (1996) 7:1226-1230.
Fischman et al., "A Randomized Comparison of Coronary-Stent Placement and Balloon Angioplasty in the Treatment of Coronary Artery Disease" The New England Journal of Medicine, (1994) 331(8):496-501.
Nakamura et al., "Technioques for Palmaz-Schatz Stent Deployment in Lesions With a Large Side Branch" Catheterization & Cardiovascular Diagnosis, (1995) 34:353-361.
Serruys et al., "A Comparison of Balloon-Expandable-Stent Implantation with Balloon Angioplasty in Patients with Coronary Artery Disease" Te New England Journal of Medicine, (1994) 331(8):489-495.
Colombo et al., "Kissing' stents for Bifurcational Lesion" Catheterization and Cardiovascular Diagnosis, (1993) 30:327-330.
Carrie et al., "T'-Shaped Stent Placement: A Technique for the Treatment of Dissected Bifurcation Lesions" Catheterization and Cardiovascular Diagnosis, (1996) 37:311-313.
Katoh et al., "New Double Wire Technique to Stent Ostial Lesions" Catheterization and Cardiovascular Diagnosis, (1997) 40:400-402.
Lewis et al., "Acute Procedural Results in the Treatment of 30 Coronary Artery Bifurcation Lesions with a Double-Wire Atherectom y Technique for Side Branch Protection" American Heart Journal, (1994) 1217:1600-1607.
U.S. Appl. No. 08/642,297, filed May 3, 1996 to Richter et al.
"Stent Jail: A Minimum-Security Prison", Caputo et al., The American Journal of Cardiology, vol. 7, Jun. 1, 1996, pp. 1226-1230, Copyright 1996 by Excerpia Medica, Inc.
Catheterization and Cardiovascular Diagnosis 30:327-330 1993 Wiley-Liss, Inc.
Progress in Cardiology Am Heart J 1994; 127:1600-7.
Catheterization and Cardiovascular Diagnosis 37:311-313 1996 Wiley-Liss Inc.
Catheterization and Cardiovascular Diagnosis 40:400-402 (1997) 1997 Wiley-Liss, Inc.
Serruys et al., The New England Journal of Medicine, vol. 331, No. 8, pp. 489-495 (1994).
Fischmann et al., The New England Journal of Medicine, vol. 331, No. 8, pp. 496-501 (1994).
Nakamura et al., Catheterization & Cardiovascular Diagnosis 34-353-361 (1995).
Caputo et al., The American Journal of Cardiology, vol. 7, pp. 1226-1230 (1996).
Colombo et al., Catheterization and Cardiovascular Diagnosis, vol. 30, pp. 327-330 (1993).
Carrie et al., Catheterization and Cardiovascular Diagnosis, vol. 37, pp. 311-313 (1996).
Katoh et al., Catheterization and Cardiovascular Diagnosis, vol. 40, pp. 400-402 (1997).
Lewis et al., American Heart Journal, vol. 127, pp. 1600-1607 (1994).
Dichek, D.A. et al.; Circulation, 80: 1347-1353 (1989).
Chevalier, B. et al.; American Journal of Cardiology, 82:943-949 (1998).
Yamashita, T. et al.; Journal of American College of Cardiology, 35: 1145-1151 (2000).
Satler, S., et al.; Catheterization and Cardiovascular Interventions, 50: 411-412 (2000).
U.S. Appl. No. 08/642,297, filed May 3, 1996, to Richter et al.
U.S. Appl. No. 09/325,996 filed Jun. 4, 1999, to Vardi et al.
U.S. Appl. No. 09/533,616 filed Mar. 22, 2000, to Vardi et al.
U.S. Appl. No. 09/614,472 filed Jul. 11, 2000, to Davidson et al.
U.S. Appl. No. 09/663,111 filed Sep. 15, 2000, to Davidson et al.
Lear et al., "The Northridge Earthquake as a Trigger for Acute Myocardial Infarction," 1 page, 1996.
SCIMED Life Systems, Inc., "TRIO 14 PTCA Catheter, Re-Engineering Over-The-Wire Balloon Technology," Brochure, 4 pages, 1994.
U.S. Appl. No. 12/136,2306, filed Jun. 10, 2008, entitled, "Side Branch Wiring Assist Sheet and Methods".
U.S. Appl. No. 12/179,960, filed Jul. 25, 2008, entitled, "Side Balloon Identifiers and Methods for Radial and Axial Alignment in a Catheter Assembly".
U.S. Appl. No. 12/184,487, filed Aug. 10, 2008, entitled, "Bifurcation Catheter Assembly Side Catheter Branch Construction and Methods".

* cited by examiner

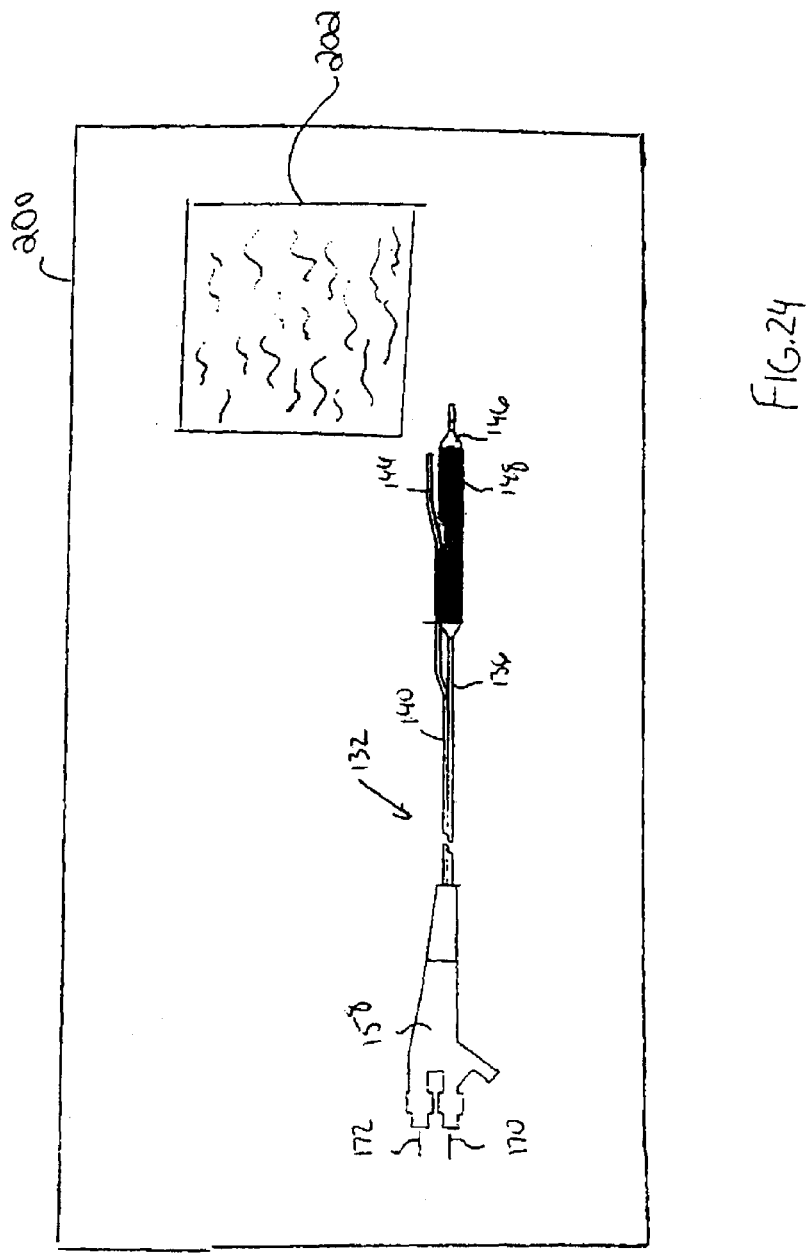

US 7,771,462 B1

CATHETER WITH SIDE SHEATH AND METHODS

CROSS-REFERENCES TO RELATED APPLICATIONS

This application is a continuation-in-part of U.S. patent application Ser. No. 09/614,472, filed Jul. 11, 2000, and entitled "CATHETER WITH SIDE SHEATH" (abandoned), which is a continuation-in-part of U.S. patent application Ser. No. 09/325,996, filed Jun. 4, 1999, and entitled "CATHETER WITH SIDE SHEATH" (abandoned), and which is a continuation-in-part of U.S. patent application Ser. No. 09/455,299, filed Dec. 6, 1999, and entitled "CATHETER WITH ATTACHED FLEXIBLE SIDE SHEATH," (now U.S. Pat. No. 6,692,483), the disclosures of which are herein incorporated by reference.

This application also is a continuation-in-part of U.S. patent application Ser. No. 09/455,299, filed Dec. 6, 1999, and entitled "CATHETER WITH ATTACHED FLEXIBLE SIDE SHEATH" (now U.S. Pat. No. 6,692,483).

This application claims priority to said Ser. Nos. 09/614,472; 09/325,996; and 09/455,299 to the extent appropriate by law.

TECHNICAL FIELD

The present invention relates to catheter systems for delivering stents.

BACKGROUND OF THE INVENTION

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al., *New England Journal of Medicine* 331: 489-495 (1994) and Fischman, D L et al. *New England Journal of Medicine* 331:496-501 (1994)). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the main vessel and/or its branches, or the bifurcation point and also limits the ability to insert a branch stent into the side branch if the result of treatment of the main, or main, vessel is suboptimal. Suboptimal results may occur as a result of several mechanisms, such as displacing diseased tissue, plaque shifting, vessel spasm, dissection with or without intimal flaps, thrombosis, and embolism.

As described in related U.S. patent application Ser. No. 08/744,002 filed Nov. 4, 1996 (now abandoned), Ser. No. 09/007,265 filed Jan. 14, 1998, now issued as U.S. Pat. No. 6,210,429, Ser. No. 08/935,383 filed Sep. 23, 1997 (now abandoned), 60/088,301 filed Jun. 5, 1998 (now expired), and PCT Patent Application No. PCT/US99/00835 filed Jan. 13, 1999, published under Publication Number WO99/36002 on Jul. 22, 1999, systems have been developed for deploying a main stent in a main vessel at the intersection of a main vessel and a branch vessel. Further, a branch stent may be positioned within a branch vessel through a side opening in the main stent. As will be appreciated, such tasks may be challenging.

For example, management of two guidewires used in introducing and/or orienting stents can pose particular challenges, such as the tendency of the guidewires to twist together. As another example, imaging placement of the stents using low-cost and convenient techniques, such as x-ray or ultrasound imaging, can be difficult using existing methods.

SUMMARY OF THE INVENTION

The invention provides systems and methods for deploying a main vessel stent in a main vessel, with a side hole in the main stent being in registry with the ostium of a branch vessel. The invention also provides techniques for positioning a branch stent in the branch vessel by passing the branch stent through the side hole of the main vessel stent. A variety of catheter designs may be employed to deploy and position the main and branch vessel stents. Such catheters may be used in connection with a pair of guidewires that terminate in the main and branch vessels. These guidewires may be used to facilitate introduction of the catheter, any stents, and/or to properly orient the stent within the vessel. For example, the branch vessel guidewire may be used alone or in combination with other elements of the catheter to assist in aligning the side hole of the main stent and/or to deploy a branch vessel stent.

In one particular embodiment, a catheter system utilizes a catheter comprising a catheter body having a distal end, a proximal end, a main vessel guidewire lumen that is adapted to receive a main vessel guidewire and a balloon disposed near the distal end of the catheter body. The catheter further comprises a side member disposed adjacent to the catheter body. The side member has a distal end, a proximal end, and a branch vessel guidewire lumen that is adapted to receive a branch vessel guidewire. A stent having a side hole is disposed over the balloon. Further, a distal portion of the side member is positioned between at least a portion of the stent and the balloon. The distal end may remain disposed beneath the stent during insertion, and then advanced through the side hole once properly positioned at the bifurcation. Alternatively, the distal end of the side member may extend out of the side hole during insertion. In either case, the distal end of the side member may be used to properly position the main vessel stent and/or to deploy a branch vessel stent.

In one aspect, such a catheter system facilitates placement of the stent within the main vessel, with the side hole being in registry with an ostium of a branch vessel. This may be accomplished, for example, by advancing a main vessel guidewire in the main vessel until passing the branch vessel. The catheter is then advanced over the main vessel guidewire until the stent reaches or is proximal to the branch vessel. At this point, a branch vessel guidewire may be introduced through the branch vessel lumen of the side member. The branch vessel guidewire is advanced out of the side member and into the branch vessel to assist in aligning the side hole with the ostium of the branch vessel prior to deployment of the stent in the main vessel. To assist in guiding the branch vessel guidewire into the branch vessel, the side member may taper to a narrow distal end, which may also be curved slightly outwardly. One advantage of such a catheter system is that a single guidewire may be used to introduce the catheter. The catheter then serves as a guide for the branch vessel guidewire.

In an alternative aspect, both of the guidewires may be inserted into the main and branch vessels to permit the catheter to be advanced over the pre-inserted guidewires. As another alternative, the catheter may be loaded onto both guidewires to permit the guidewires and the loaded catheter to be introduced as a combined system. In such a case, the system may be advanced until reaching the end of a guide catheter. The guidewires may then be advanced out of the guide catheter and into the main and branch vessels. With the guidewires in place, the catheter may be further advanced to force the side member into the branch vessel and to align the side hole with the ostium of the branch vessel. In cases where the distal tip of the catheter is sufficiently flexible, the catheter may be advanced to the vessel bifurcation before extending the guidewires.

Alignment of the side hole with the ostium may be accomplished in a variety of ways. For example, introduction of the branch vessel guidewire into the branch vessel may sufficiently align the side hole with the ostium. Other alignment techniques may depend on the configuration of the side member. For example, in some cases the side member may comprise a flexible sheath that is movably coupled to the catheter body, e.g., by passing through a lumen of a truncated connector that is coupled to the catheter body. Once the branch vessel guidewire is advanced into the branch vessel, the sheath may be advanced into the branch vessel to move the side hole into registry with the ostium. Conveniently, the catheter body and the side member may be fabricated from pebax and graphite to facilitate relative movement between the catheter body and the side member.

In other cases, the flexible sheath may be fixedly coupled to the catheter body, except at the distal end. For example, the length over which the distal end of the side member is unattached to the distal end of the main catheter may be approximately 2 to approximately 10 cm to aid with the final rotation of the stent body for alignment with the ostium without compromising the pushability of the delivery system. With this configuration, once the branch vessel guidewire is in place, the catheter may be further advanced over both guidewires, with the distal end of the side member extending further into the branch vessel, thereby aligning the side hole with the ostium in the three dimensional space.

A variety of techniques may be used to ensure that the distal end of the side member is properly advanced into the branch vessel. For example, the side hole in the main vessel stent may be aligned with the ostium of the branch vessel by viewing relative movement of radiopaque markers positioned on the catheter body and the side member. The relative marker movement indicates that the distal portion of the side member is advancing into the ostium of the branch vessel over the branch vessel guidewire while the catheter body proceeds through the main vessel.

Such relative movement of the radiopaque markers may be viewed as a rotation of a marker positioned on the side member with respect to one or more markers positioned on the catheter body, or as a separation between the marker on the side member with respect to one or more markers on the main catheter. In one aspect, markers may be positioned at the distal ends of the side member and the catheter body, such that the separation between these markers will be relatively large, and thus can be easily viewed. Moreover, when the markers are positioned at the distal ends of the main vessel stent and side member, the surgeon will view the separation of these markers earlier than would be the case if these markers were disposed at a more proximal location.

Conveniently, a plurality of markers may be positioned on the catheter body, with markers positioned at locations corresponding to the proximal and distal ends of the main vessel stent. A medial marker may also be included, positioned somewhere halfway between the distal and proximal markers, for indicating the position of the side hole in the main vessel stent, (which may be positioned anywhere between the distal and proximal ends of the stent).

The relative movement of the markers positioned on the catheter body and those positioned on the side member may be observed fluoroscopically. Conveniently, the markers may be constructed of radiopaque materials, such as tungsten, platinum or gold. In one option, the distal end of the side member may be fabricated from a fluoroscopically visible material, such as tungsten.

Once the stent is properly positioned, the balloon may be inflated to deploy the stent. Conveniently, the catheter body may include a balloon inflation lumen to permit the balloon to be inflated.

In another aspect, the catheter system may be used to deploy a branch vessel stent within the branch vessel following deployment of the main vessel stent. A variety of techniques may be used to deploy the branch vessel stent. For example, if the side member is slidably coupled to the catheter body, the side member may be provided with a balloon at the distal end, with the branch stent being coupled over the balloon. In this way, the side member may be advanced into the branch vessel and the balloon inflated to deploy the branch stent. As another example, the side member may be retracted from the main vessel while the branch vessel guidewire is kept in place. A stent deployment device having a balloon and a branch stent disposed over the balloon may then be advanced over the branch guidewire and into the branch stent. The branch stent may then be deployed by inflating the balloon. In another option, the main vessel stent may be only partially expanded to permit the branch stent to be deployed through the main vessel stent. Once the branch vessel stent is in place, the main vessel stent may be fully deployed.

In cases where the side member is fixedly attached to (or integrally formed with) the catheter body, the distal end of the side member may include a balloon, with the branch stent being disposed over the balloon. The catheter may be advanced over the two guidewires until the branch stent is distally positioned within the branch vessel. The main stent may then be deployed, and the entire device pulled back until the branch stent is appropriately positioned. The balloon on the side member may then be inflated to deploy the branch stent. In another option, the entire catheter may be withdrawn from the patient while at least the branch guidewire is left in place. A stent deployment device may then be advanced into the branch vessel in a manner similar to that just described.

In one particular aspect, the catheter system may further include a proximal end hub having a main vessel guidewire channel that is coupled to the main vessel guidewire lumen, a branch vessel guidewire channel that is coupled to the branch vessel guidewire lumen, and a balloon inflation port that is coupled to the balloon inflation lumen. In one aspect, the first and second guidewire channels may be separated by about zero to about 20° to aid wire movement without hindering device preparation for use. For example, such an angle facilitates the attachment of syringes while also ensuring that the guidewires are not too separated.

The main vessel stent may optionally include outwardly expandable portions which can be expanded from an initial position which is flush with the cylindrical body of the stent to protrude outwardly from the side hole. Such a configuration may be used to anchor the stent into the walls of the branch vessel to hold the side opening in registry with the ostium of the branch vessel. In an exemplary aspect, the cylindrical body of the main vessel stent may have an even surface and an expandable portion that is positioned within the side hole of the cylindrical body, such that the expandable portion is flush with the cylindrical body prior to expansion.

In one aspect, the branch stent may optionally comprise a contacting portion at its proximal end to secure the proximal end of the branch stent to the side hole in the main vessel stent. In an exemplary aspect, the contacting portion comprises a flared proximal end.

BRIEF DESCRIPTION OF THE DRAWINGS

FIG. 24 illustrates a kit having the catheter of FIG. 21 and a set of instructions for using the catheter.

DESCRIPTION OF THE SPECIFIC EMBODIMENTS

The present invention provides systems and methods for positioning a pair of guidewires in main and branch vessels at a vessel bifurcation to facilitate positioning and deployment of one or more stents, such as a main vessel stent or a branch vessel stent. The systems and methods may also be used to align a side hole in a main vessel stent in registry with the ostium of a branch vessel.

Applications of the invention include the cardiac, coronary, renal, peripheral vascular, gastrointestinal, pulmonary, urinary and neurovascular systems and the brain. Advantages of the invention include, but are not limited to, the use of an improved stent delivery apparatus, which may deliver main vessel and branch vessel stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a main stent is implanted; 4) treat bifurcation lesions in a bifurcated vessel where the branch vessel extends from the side of the main vessel; and 5) be marked with, or at least partly constructed of, material which is imageable by commonly used intraluminal catheterization visualization techniques including but not limited to ultrasound or x-ray.

As described herein, a side hole in the main vessel stent refers to a relatively large hole which is intended to be aligned with the ostium of the branch vessel. Such a side hole is separate from any of the multiple passageways extending through the side of the stent between struts in the stent geometry. Accordingly, the side hole in the stent is a hole which is understood to be larger than other passages through the stent. In some aspects, this side hole is defined by a band of continuous material which defines the perimeter of the side hole. This continuous band of material preferably comprises discontinuities over its length so that the area of the side hole expands together with the expansion of the stent. In various aspects, the continuous band comprises protrusions which project inwardly from a peripheral edge of the side opening. Preferably, these protrusions (or expandable portions) are initially aligned within a cylindrical envelope of the tubular body of the stent.

Figure 1:
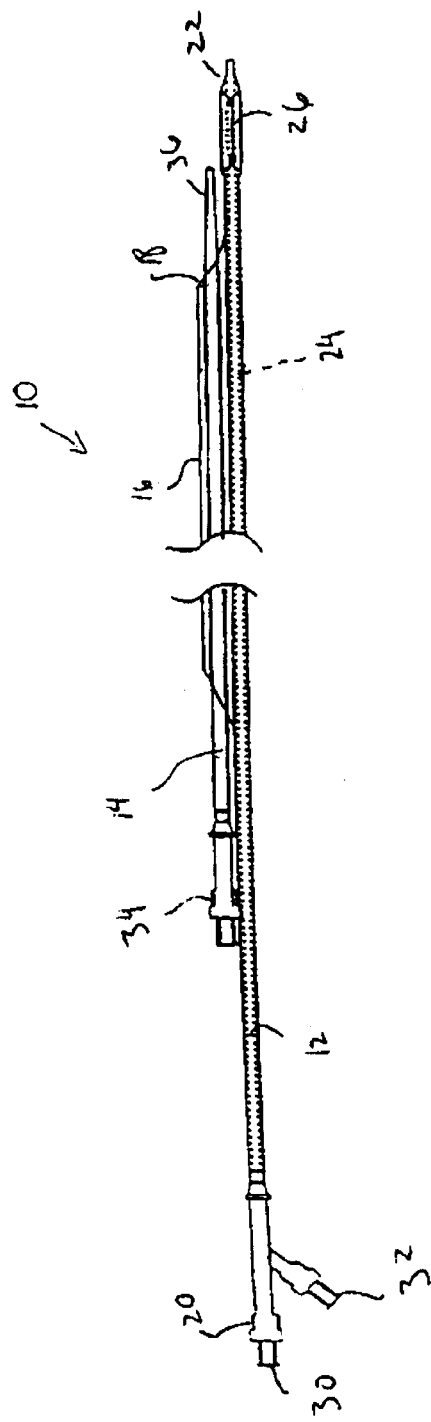
FIG. 1 illustrates one embodiment of a catheter having a catheter body and a side member movably coupled to the catheter body according to the invention.

Referring now to FIG. 1, one embodiment of a catheter 10 will be described. Catheter 10 comprises a catheter body 12 and a side member 14 that is adjacent to catheter body 12. Integrally formed with catheter body 12 is a connector 16 having a lumen 18 into which side member 14 is slidably received. In this way, side member 14 is movable with respect to catheter body 12. To facilitate sliding of side member 14 in lumen 18, connector 16 may be constructed of pebax with graphite. Alternatively, the inner surface of lumen 18 may have metal powders, glass beads, Teflon power, imbedded inorganic fibers, or the like.

Figure 3:
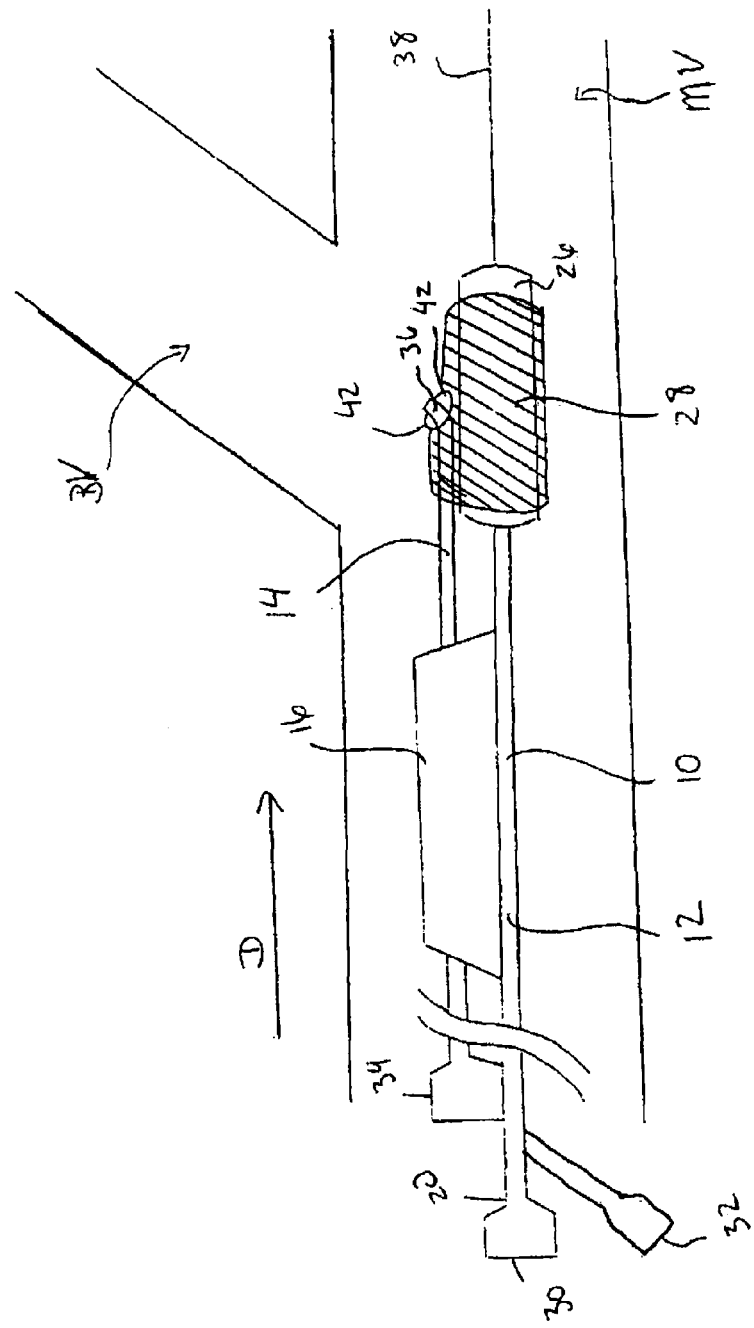
FIG. 3 illustrates the advancement of the catheter of FIG. 1 over the guidewire of FIG. 2.

Catheter body 12 has a proximal end 20 and a distal end 22. Extending between proximal end 20 and distal end 22 is a guidewire lumen 24 to permit a guidewire to be inserted through catheter body 12. Catheter body 12 is constructed of a flexible material to permit catheter body 12 to traverse through vessels in the body. An annular balloon inflation lumen (not shown) is disposed about guidewire lumen 24 to permit a balloon 26 at distal end 22 to be inflated. As illustrated in FIG. 3, a stent 28 (omitted from FIG. 1 for convenience of illustration) is crimped about balloon 26. In this way, balloon 26 may be inflated to deploy stent 28. At proximal end 20 is a guidewire port 30 that leads to guidewire lumen 24, and a balloon inflation port 32 that leads to the balloon inflation lumen.

Side member 14 has a proximal end 34 and a distal end 36. Extending between proximal end 34 and distal end 36 is a guidewire lumen (hidden from view) that is configured to receive a branch vessel guidewire. Side member 14 is constructed as a flexible sheath to permit side member 14 to navigate through a patient's vessels. Conveniently, distal end 36 may be tapered to facilitate introduction of distal end 36 into a branch vessel.

Catheter 10 may be used to introduce a stent into a main vessel, with a side hole of the stent being aligned with an ostium of a branch vessel. Optionally, catheter 10 may also be used to facilitate the introduction of a branch stent into a branch vessel. To accomplish such tasks, catheter 10 utilizes a pair of guidewires, conveniently referred to as main vessel and branch vessel guidewires, that terminate in a main vessel and a branch vessel of a patient. A variety of techniques may be used to introduce the guidewires and catheter 10 into the patient. For example, the main vessel guidewire may first be introduced into the main vessel. Catheter 10 may then be loaded onto the main vessel guidewire and introduced into a patient. Once in place, the branch vessel guidewire may be passed through the guidewire lumen of side member 14. As an alternative, both guidewires may initially be introduced into the patient. Catheter 10 may then be loaded onto both guidewires and introduced into the patient. As a further alternative, catheter 10 may be loaded onto both guidewires such that the distal ends of the guidewires extend slightly past distal ends 22 and 36. Catheter 10 and the guidewires may then be introduced into the patient as a single unit.

Figure 2:
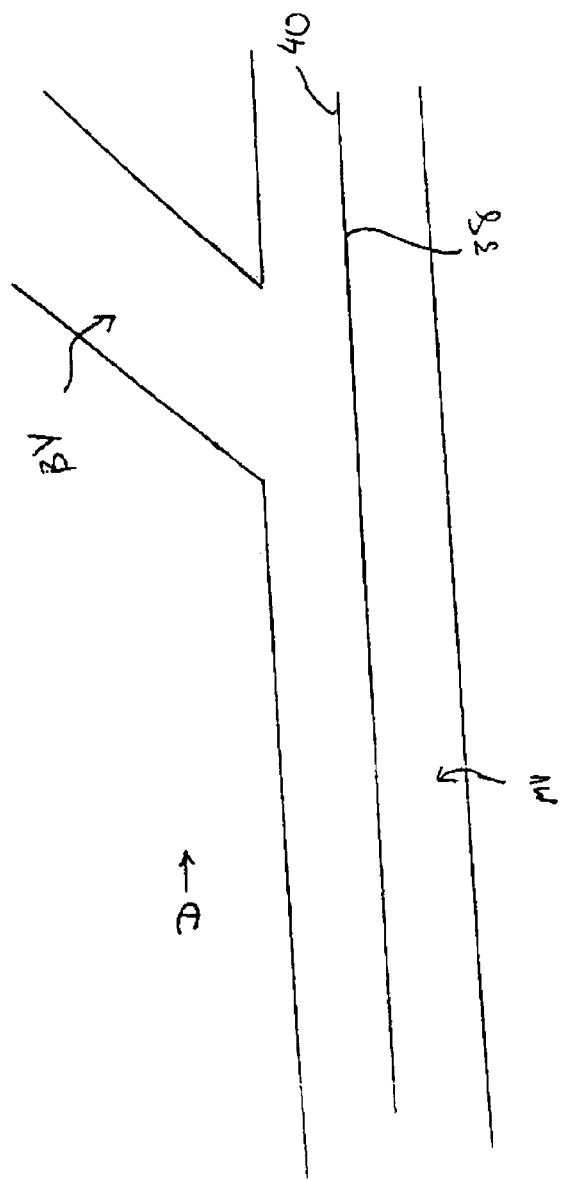
FIG. 2 illustrates the placement of a main vessel guidewire into a main vessel according to the invention.
Figure 4:
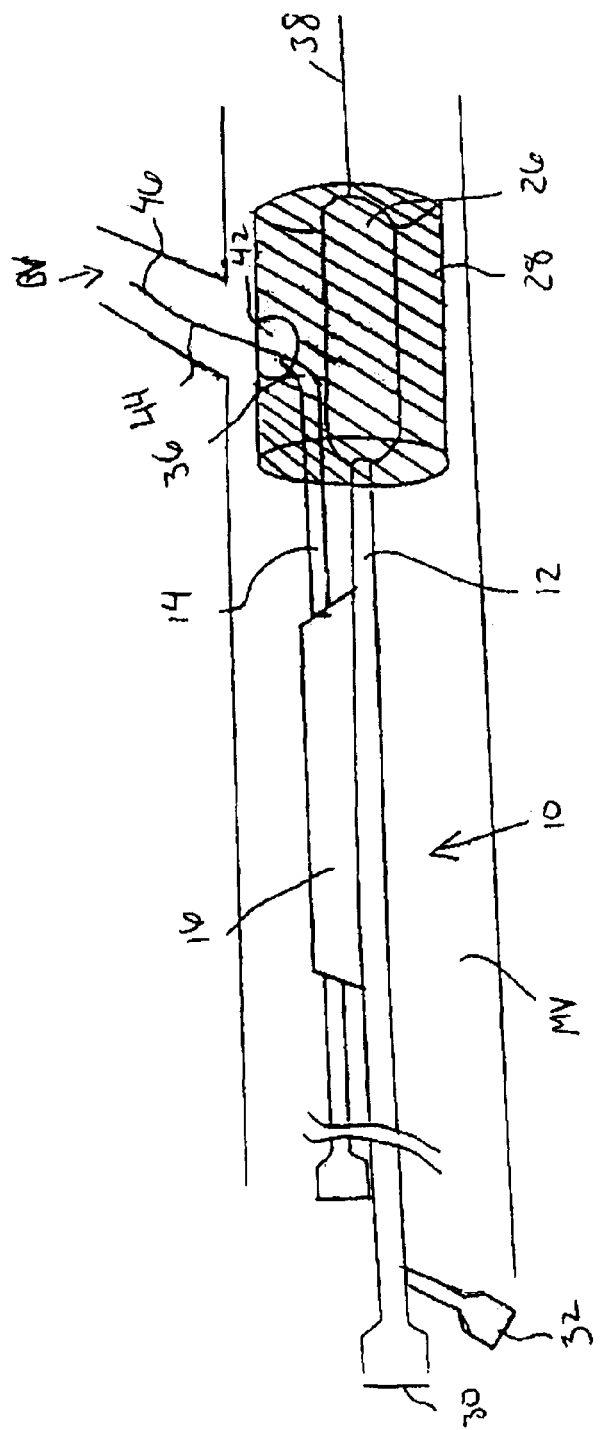
FIG. 4 illustrates the catheter of FIG. 1 after a branch vessel guidewire has been introduced through the side member and into a branch vessel.

Referring now to FIGS. 2-4, one method of introducing stent 36 into a main vessel MV of a patient will be described. Initially, a main vessel guidewire 38 is inserted into main vessel MV using techniques known in the art (see FIG. 2). Guidewire 38 is moved in a direction D until a distal end 40 of guidewire 38 extends beyond the intersection of main vessel MV and a branch vessel BV.

As shown in FIG. 3, catheter 10 is loaded onto guidewire 38 such that guidewire 38 passes through lumen 24 and is advanced in direction D until stent 28 reaches the ostium of branch vessel BV. Stent 28 includes a side hole 42 that is placed in the vicinity of the ostium of branch vessel BV. Stent 28 is crimped to balloon 26 such that distal end 36 of side member 14 is positioned between stent 28 and balloon 26 and terminates at side hole 42. In this way, distal end 36 is stored beneath stent 28 to permit catheter 10 to be routed through main vessel MV without interference from distal end 36 and while using only a single guidewire.

To facilitate alignment of side hole 42 with the ostium of branch vessel BV, distal end 36 may include tungsten or another radiopaque material to permit fluoroscopic visualization. Hence, a surgeon may stop advancement of catheter 10 when distal end 36 (as viewed under fluoroscopy) reaches branch vessel BV.

As shown in FIG. 4, a branch vessel guidewire 44 may be advanced through the lumen of side member 14 until a distal end 46 passes through side hole 42 and into branch vessel BV. In this way, guidewire 44 may be used to align side hole 42 of stent 28 with the ostium of branch vessel BV. Once properly aligned, balloon 26 may be inflated to deploy stent 28.

Optionally, distal end 36 of side member may be advanced over guidewire 44 and into branch vessel BV before stent 28 is fully displayed to further assist in aligning side hole 42 with the ostium. Further, although the method for deploying stent 28 has been described using a single guidewire to introduce catheter 10 into the patient, it will be appreciated that both guidewires may be used as previously described.

Figure 5:
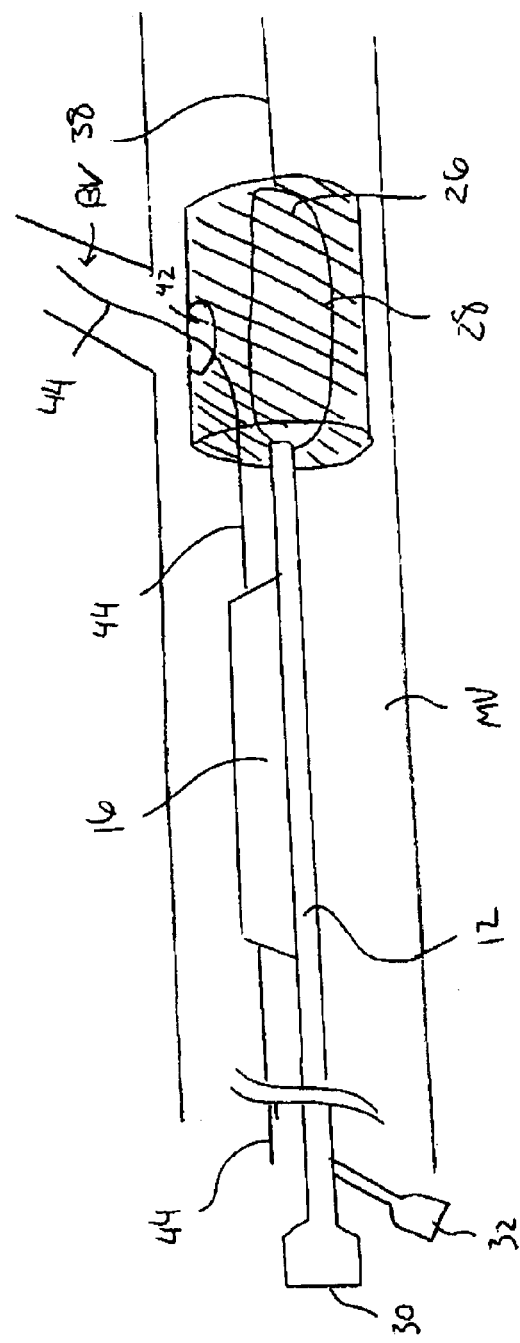
FIG. 5 illustrates the catheter of FIG. 1 after the branch guidewire has been introduced into the branch vessel, and after the side member has been withdrawn.
Figure 6:
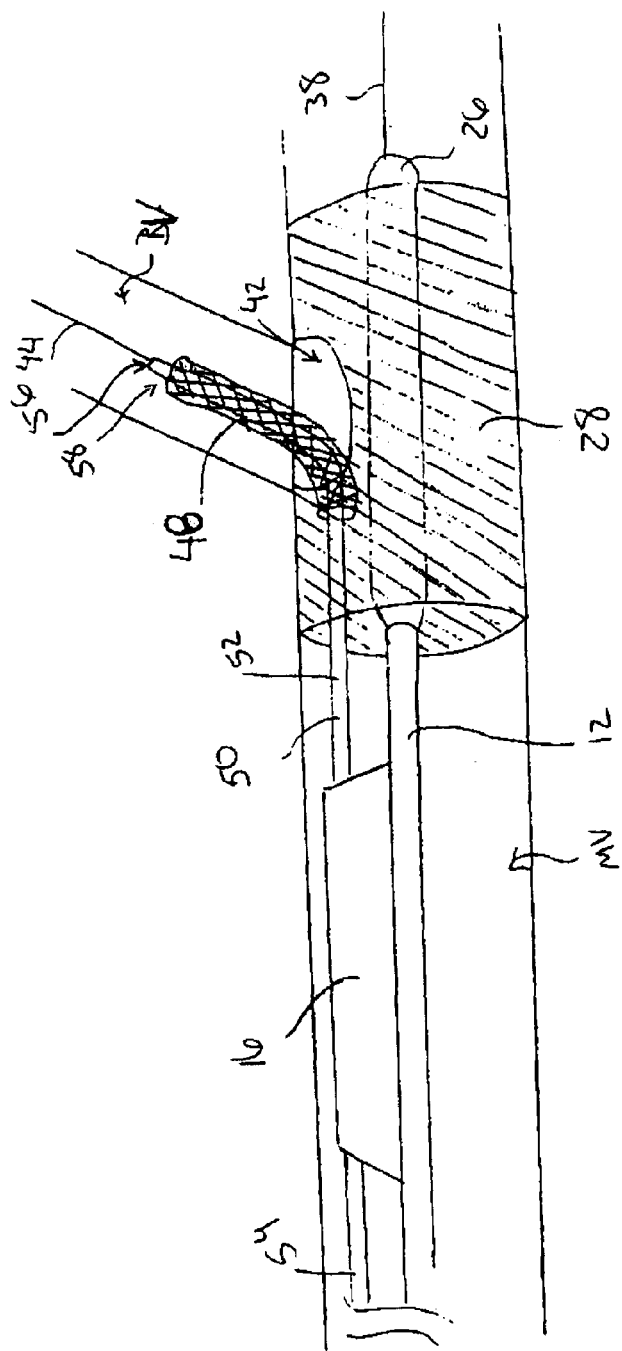
FIG. 6 illustrates the introduction of a branch stent deployment device over the branch vessel guidewire after the main stent is deployed.
Figure 7:
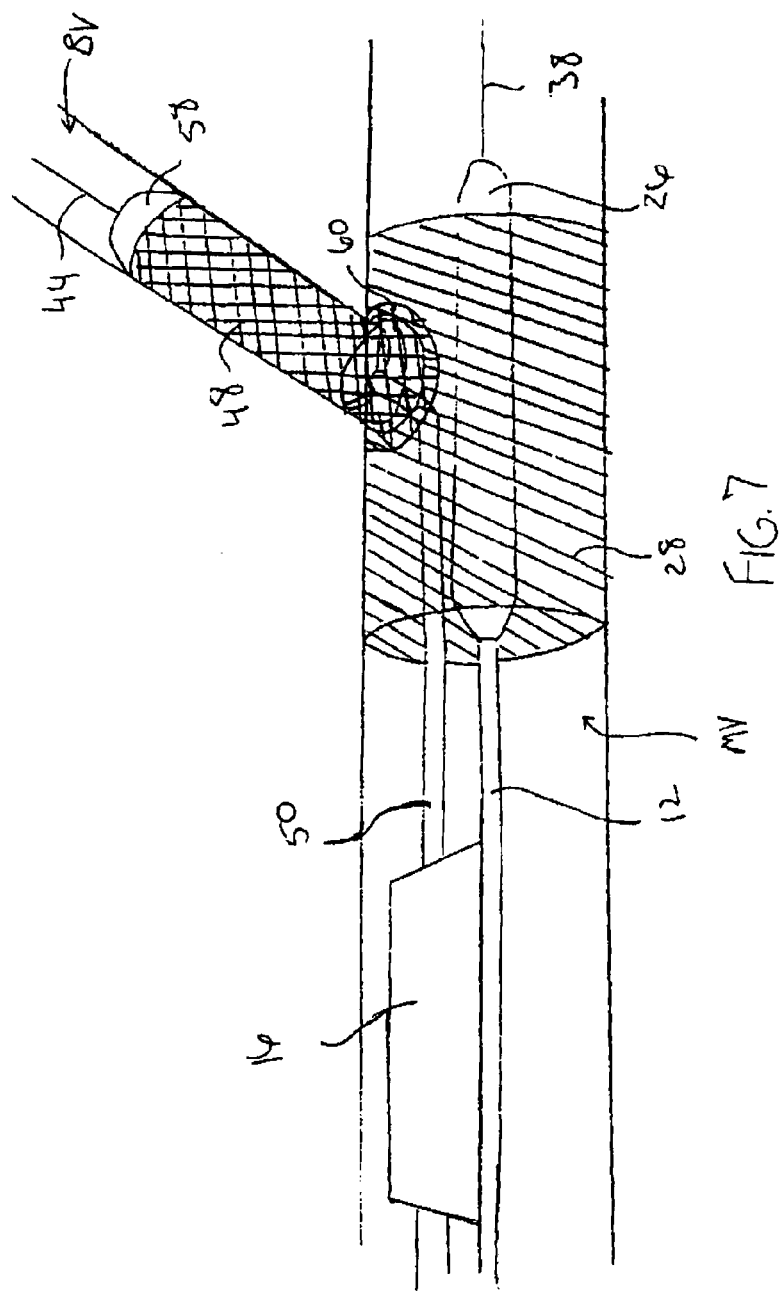
FIG. 7 illustrates the deployment of a branch stent using the deployment device of FIG. 6.
Figure 8:
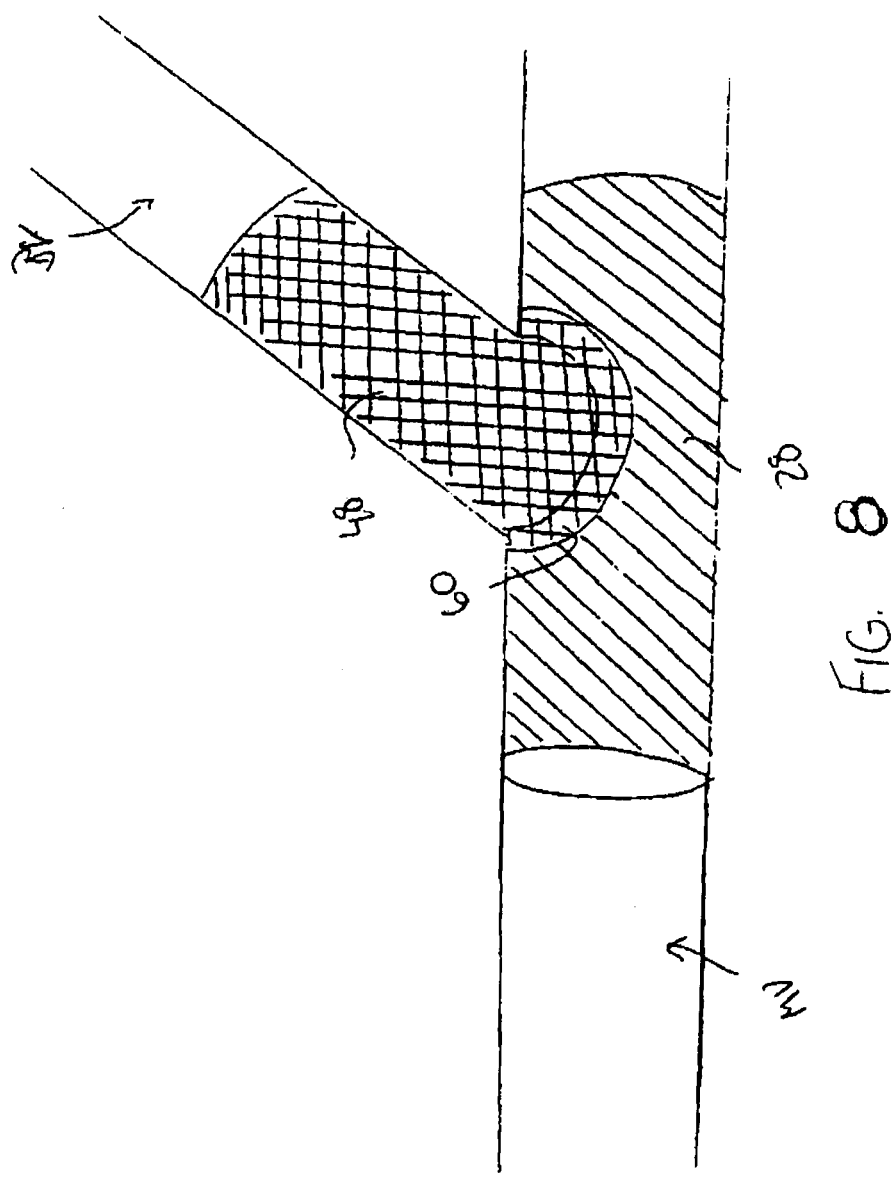
FIG. 8 illustrates an alternative catheter having a catheter body and a side member with a balloon at a distal end.

With stent 28 partially or fully deployed, catheter 10 may be used to facilitate the deployment of a branch vessel stent 48 as illustrated in FIGS. 5-7. As shown in FIG. 5, side member 14 is withdrawn from main vessel MV, leaving branch vessel guidewire 44 in place. As shown in FIG. 6, a stent deployment device 50 having a branch vessel stent 48 attached thereto is introduced over branch vessel guidewire 44 until branch vessel stent 48 extends out of side hole 42. Stent deployment device 50 comprises an elongate flexible body 52 having a proximal end 54 and a distal end 56. Extending between proximal end 54 and distal end 56 is a guidewire lumen to permit body 52 to be inserted over guidewire 44. Disposed at distal end 56 is a balloon 58 over which stent 48 is positioned. Flexible body 52 further includes a balloon inflation lumen to permit balloon 58 to be inflated from outside of the patient. Once branch vessel stent 48 extends into branch vessel BV, balloon 58 may be inflated to deploy branch vessel stent 48 within branch vessel BV as illustrated in FIG. 7. Optionally, branch vessel stent 48 may include a contact portion 60 that remains disposed within stent 28 to secure a proximal end of branch vessel stent 48 to side hole 42 of stent 28. In this way, a bifurcated stent arrangement is provided which extends both into the main vessel MV and branch vessel BV. After main vessel stent 28 and branch vessel stent 48 have been deployed, catheter body 12 and stent deployment device 50 may be withdrawn from the patient leaving a bifurcated support at the intersection of main vessel MV and branch vessel BV as illustrated in FIG. 8.

Figure 9:
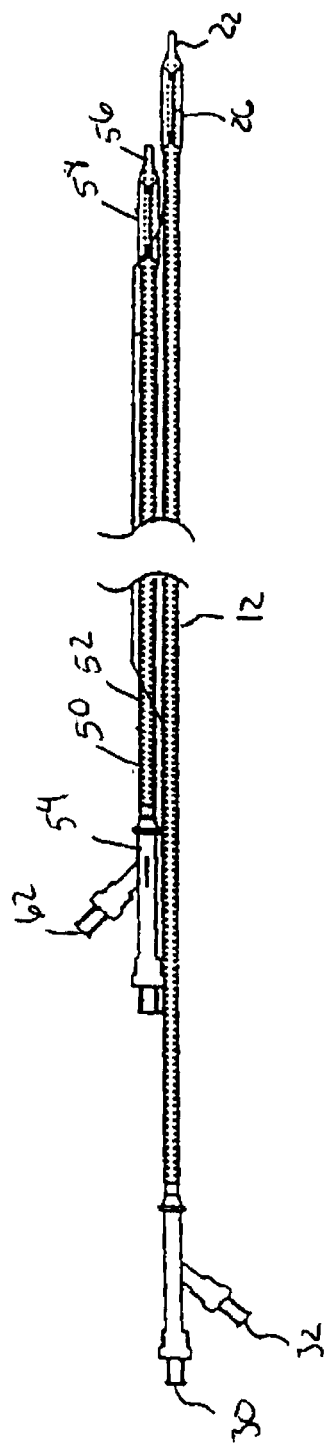
FIG. 9 illustrates the catheter body and stent deployment device of FIG. 6.

As an alternative to using catheter body 12 and side member 14 in combination with stent deployment device 50 to deploy branch vessel stent 48 in combination with main vessel stent 28, catheter body 12 may be used in combination with stent deployment device 50 alone to accomplish such features. A combination of stent deployment device 50 with catheter body 12 is illustrated in FIG. 9. For convenience of illustration, both main vessel stent 28 and branch vessel stent 48 have been omitted from view. With such a configuration (as shown in FIG. 6), catheter body 12 and stent deployment device 50 may be introduced into the patient over guidewires 38 and/or 44 using any of the techniques previously described. After stent 28 has been introduced into the area of bifurcation, guidewire 44 and/or distal end 56 of stent deployment device 50 may be used to align side hole 42 with the ostium of branch vessel BV. Distal end 56 of stent deployment device 50 may be positioned within branch vessel BV in a manner similar to that described in connection with FIG. 7. Branch vessel stent 48 may then be deployed in a manner similar to that previously described by inflating balloon 58 using a balloon inflation port 62. In this way, branch vessel stent 48 may be deployed without having to withdraw side member 14 prior to introduction of stent deployment device 50.

Figure 10:
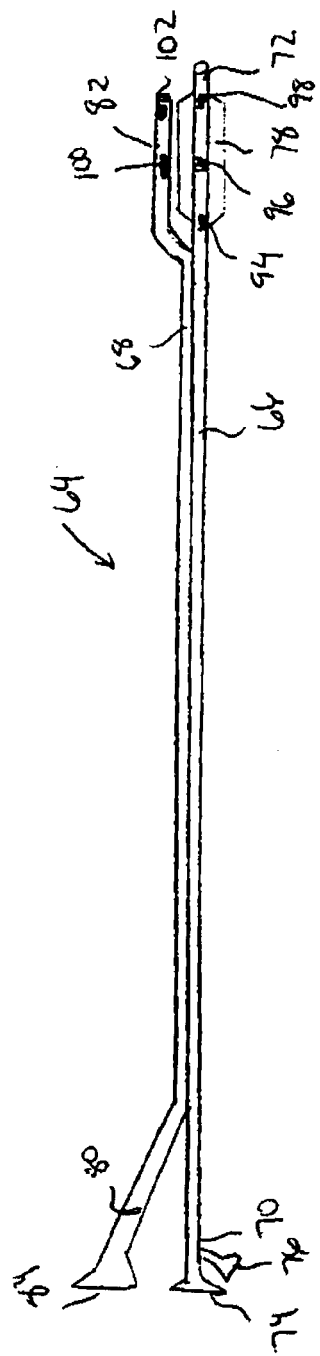
FIG. 10 illustrates an alternative embodiment of a catheter having a catheter body and a side member that is fixably attached to the catheter body according to the invention.

Referring now to FIG. 10, another embodiment of a stent delivery catheter 64 will be described. Catheter 64 comprises a catheter body 66 and a side member 68 that is attached to catheter body 66. Both catheter body 66 and side member 68 are constructed of a flexible material to permit catheter 64 to traverse through the tortious vessels of the human body. Catheter body 66 has a proximal end 70 and a distal end 72. Extending between proximal end 70 and distal end 72 is a guidewire lumen (hidden from view) for receiving a guidewire. At the proximal end 70 is a guidewire port 74 and a balloon inflation port 76. Also extending through catheter body 66 is a balloon inflation lumen that permits a balloon 78 at distal end 72 to be inflated using balloon inflation port 76.

Side member 68 has a proximal end 80 and a distal end 82. Extending between proximal end 80 and distal end 82 is a guidewire lumen (hidden from view) for receiving another guidewire. Side member 68 is fixably attached to catheter body 66 except at distal end 82 where side member 68 is separated from catheter body 66. Conveniently, catheter body 66 and side member 68 may be formed as an integral unit. In one aspect, the portion of distal end 82 that is detached from catheter body 66 is in the length from about 2 cm to about 10 cm. Side member 68 may further include a guidewire port 84 to facilitate introduction of a guidewire into the guidewire lumen.

Figure 11:
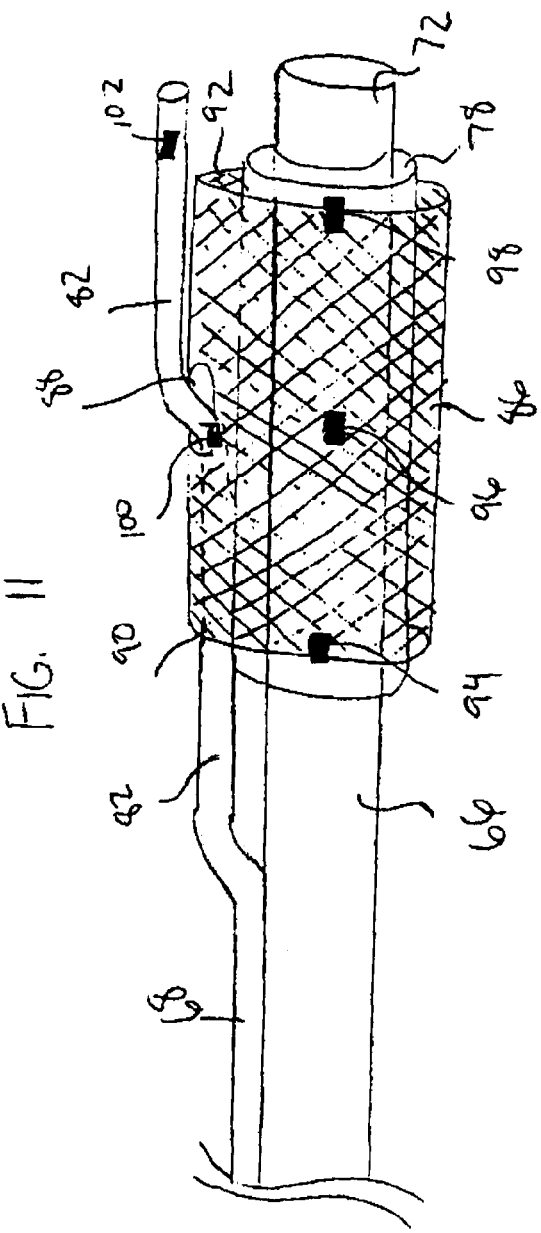
FIG. 11 is a more detailed view of a distal end of the catheter of FIG. 10.

As best shown in FIG. 11, a main vessel stent 86 is crimped about balloon 78. In this way, main vessel stent 86 may be deployed upon inflation of balloon 78. As further illustrated in FIG. 11, main vessel stent 86 includes a side hole 88 that may be aligned with an ostium of a branch vessel in a manner similar to that previously described with other embodiments. Main vessel stent 86 further includes a proximal end 90 and a distal end 92. Distal end 82 of side member 68 passes between stent 86 and balloon 78 at proximal end 90. Distal end 82 of side member 68 further extends through side hole 88 so that it is outside of stent 86. Such a configuration permits distal end 82 to be advanced into a branch vessel prior to deployment of main vessel stent 86 to facilitate alignment of side hole 88 with the ostium of the branch vessel.

Figure 12:
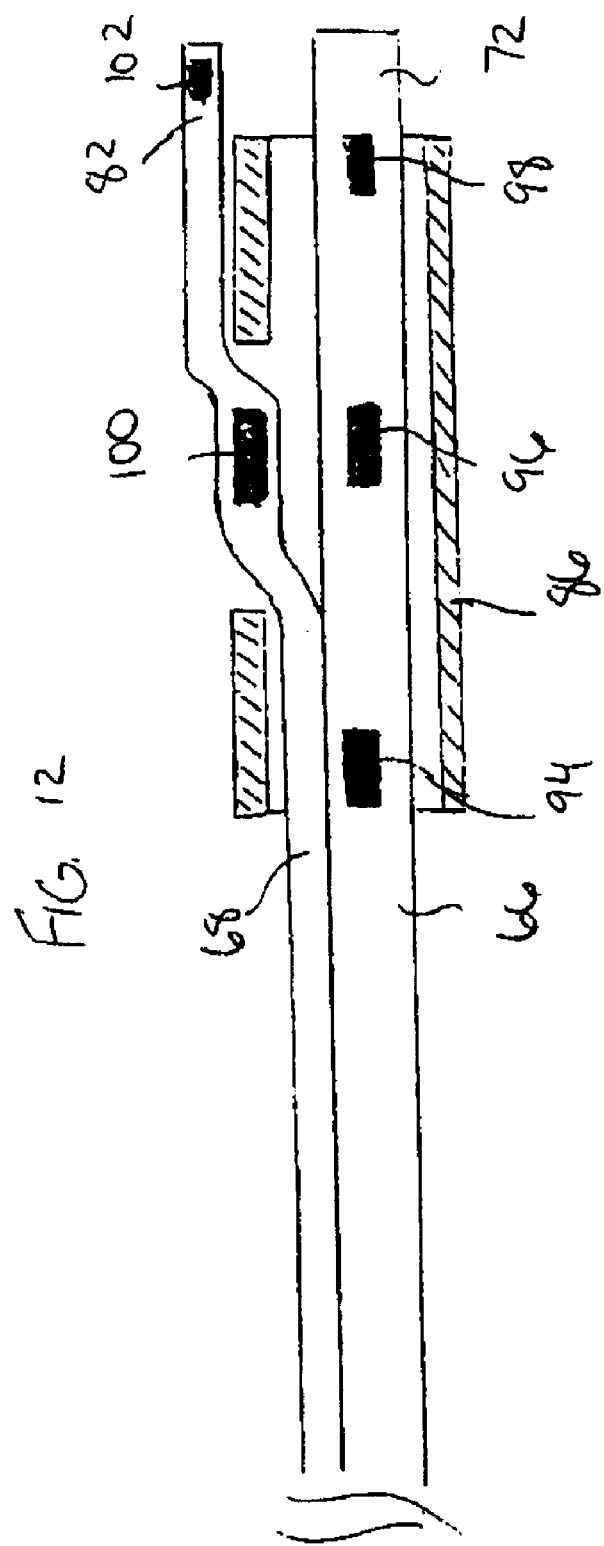
FIG. 12 is a cross sectional side view of the distal end of the catheter of FIG. 11.
Figure 13:
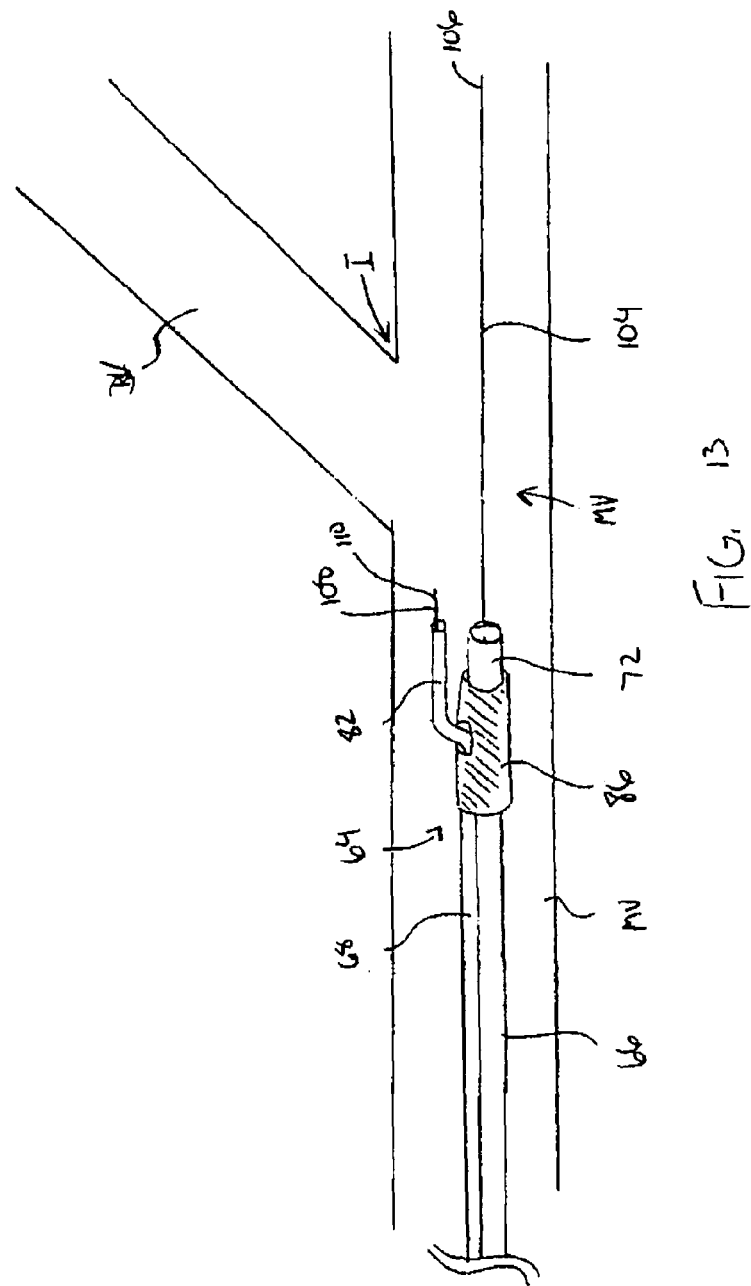
FIG. 13 illustrates the introduction of the catheter of FIG. 10 into a main vessel according to the invention.

Catheter 64 further includes a proximal marker 94, a medial marker 96 and a distal marker 98 that are disposed on catheter body 66. Conveniently, the location of proximal marker 94 may correspond to the location of proximal end 90 of stent 86. The location of distal marker 98 may correspond to the location of distal end 92 of stent 86. Further, the location of medial marker 96 may correspond to the location of side hole 88. Side member 68 may further include at least one marker that is positioned on distal end 82. As shown, a marker 100 is aligned with side hole 88, and a marker 102 is aligned with distal end 92 of stent 86. Each of the markers may be constructed of a fluoroscopically visible material to permit visualization of the markers during a deployment procedure. As described in greater detail hereinafter, use of markers on both catheter body 66 and side member 68 provides the surgeon with information as to when distal end 82 is entering into a branch vessel while distal end 72 of catheter body 66 is advancing further into the main vessel. Conveniently, each marker may be slightly elongated and rectangular in shape. Examples of materials that may be used to construct the markers include tungsten, gold or the like. A more detailed view of the markers is illustrated in FIG. 12.

Referring now to FIGS. 13-16, one method for introducing stent 86 into a main vessel, with side hole 88 being aligned with an ostium of a branch vessel, will be described. Initially, a main vessel guidewire 104 is introduced into main vessel MV until a distal end 106 extends past a vessel intersection I between branch vessel BV and main vessel MV. Catheter 64 is then loaded onto guidewire 104 and introduced into main vessel MV, with guidewire 104 extending through the guidewire lumen of catheter body 66. A branch vessel guidewire 108 is also introduced into side member 68 such that a distal end 110 of branch vessel guidewire 108 extends beyond distal end 82 of side member 68. In this way, distal end 82 has sufficient rigidity to track through main vessel MV. Alternatively, branch vessel guidewire 108 could be introduced into main vessel MV until distal end 110 extends into branch vessel BV. Catheter 64 may then be loaded onto both guidewires and tracked over both guidewires until in the position shown in FIG. 13. As another alternative, catheter 64 may be loaded onto guidewires 104 and 108 such that distal ends 106 and 110 extend just distally of catheter 64. Catheter 64 and guidewires 104 and 108 may then be simultaneously introduced upon to the distal edge of a guiding catheter where the guidewires may then be advanced.

Figure 14:
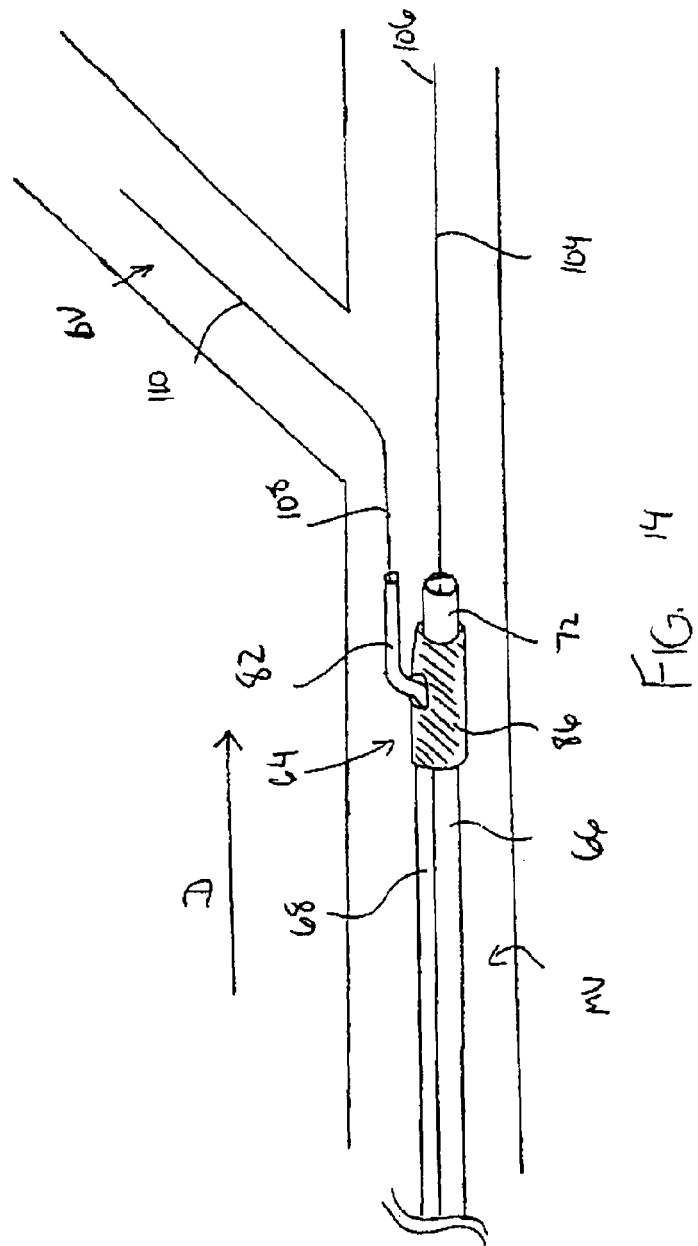
FIG. 14 illustrates the advancement of a branch vessel guidewire into a branch vessel using the catheter of FIG. 10.

As shown in FIG. 14, prior to deployment of main vessel stent 86, distal end 110 of branch vessel guidewire 108 is positioned into branch vessel BV. This may be accomplished, for example, by advancing guidewire 108 out of distal end 82 until reaching branch vessel BV. As previously described, branch vessel guidewire 108 may be preinserted into branch vessel BV so that such an advancing step is not needed. As catheter 64 is further advanced into main vessel MV in the direction of arrow D, branch vessel guidewire 108 serves to align side hole 88 with the ostium of branch vessel BV. Further, distal end 82 of side member 68 passes into branch vessel BV to further ensure alignment of side opening 88 with the ostium of branch vessel BV.

Figure 15:
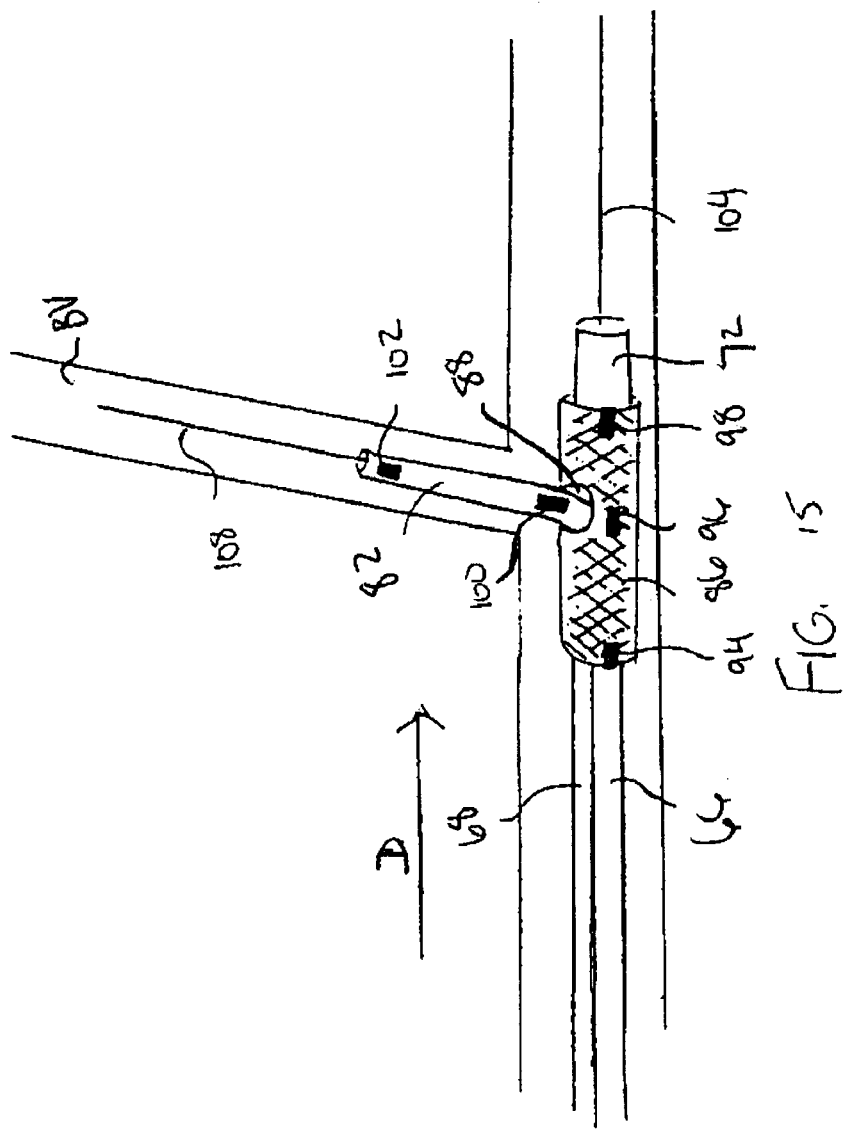
FIG. 15 illustrates the introduction of a distal end of the side member into the branch vessel to facilitate alignment of a side hole with the ostium of the branch vessel.
Figure 16:
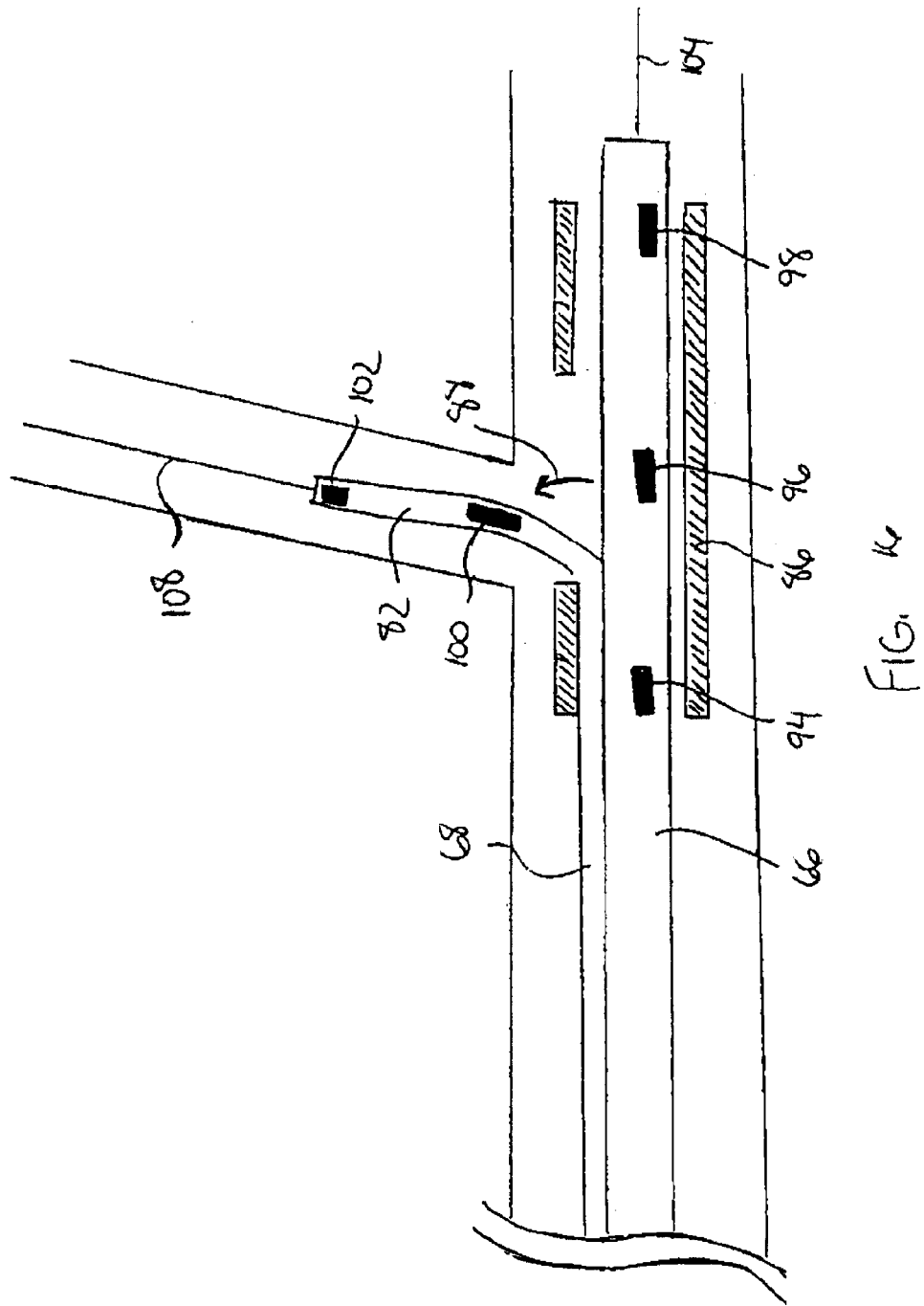
FIG. 16 is a cross sectional view of the catheter of FIG. 15.

As shown in FIGS. 15 and 16, catheter 64 is advanced into main vessel MV, and fluoroscopic viewing equipment may be used to fluoroscopically view markers 94, 96, 98, 100 and 102. Movement of markers 100 and 102 relative to markers 94, 96 and 98 is an indicator that distal end 82 is advancing into branch vessel BV while catheter body 66 is advancing in the main vessel MV. For example, as distal end 82 begins to enter into branch vessel BV, markers 100 and 102 will begin to separate from markers 94, 96 and 98. In many cases, branch vessel BV will not be aligned in the same plane as main vessel MV. As such, distal end 82 will rotate relative to distal end 72 of catheter body 66. Use of multiple markers on both distal end 82 and distal end 72 facilitates fluoroscopic visualization of relative movement of the markers when distal end 82 is rotating as it enters into branch vessel BV. Further, by viewing the position of markers 94, 96, and 98, the operator may determine the position of proximal end 90 and distal end 92 of stent 86, as well as the position of side hole 88 with respect to the ostium of branch vessel BV.

Once proper alignment has been determined, balloon 78 may be inflated to deploy stent 86 within the main vessel. Catheter 64 may then be removed from the patient, with stent 86 remaining in position.

Figure 17:
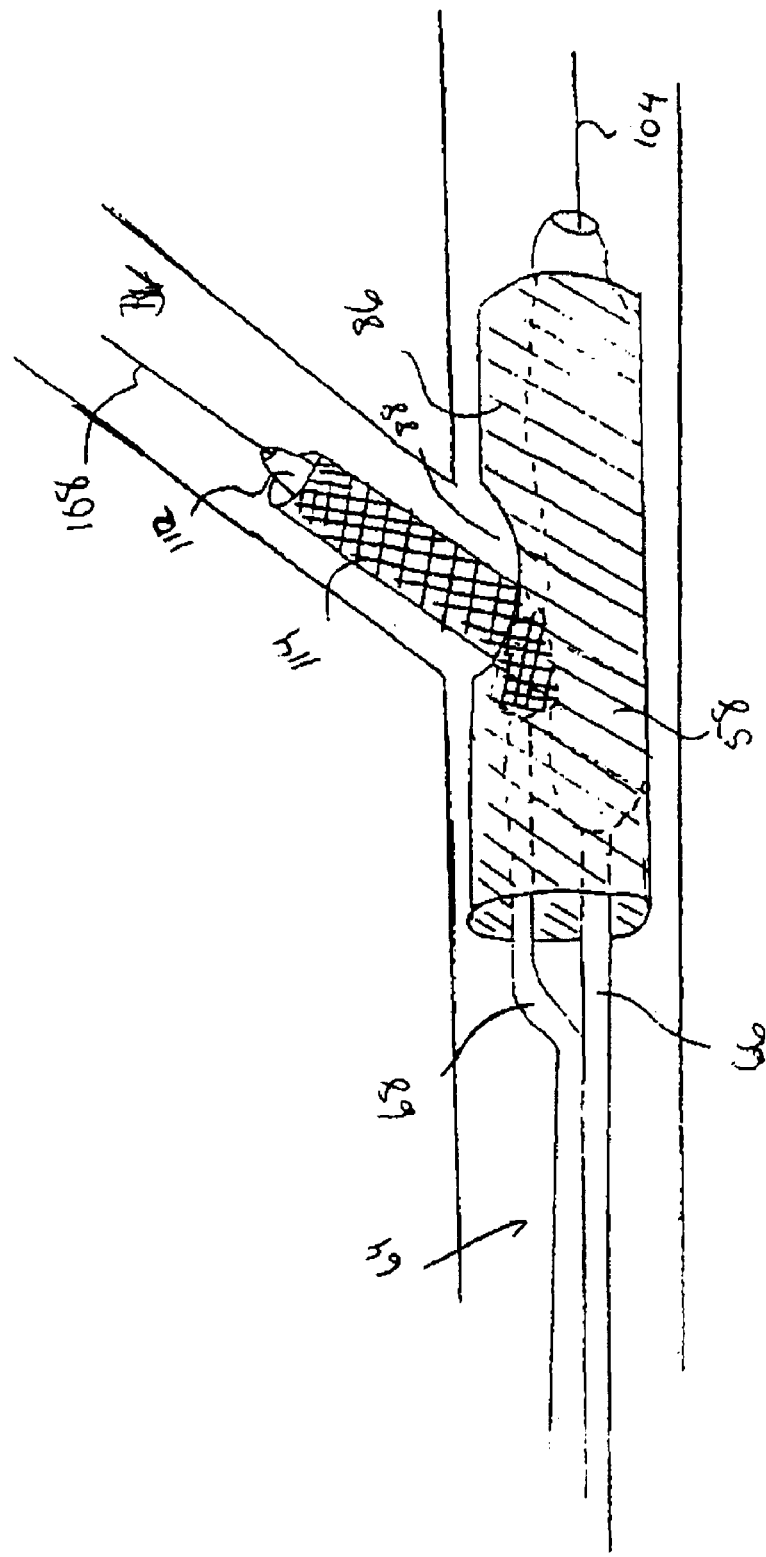
FIG. 17 illustrates the deployment of a branch vessel stent into a branch vessel using the catheter of FIG. 10 with a modified side member according to the invention.

As shown in FIG. 17, catheter 64 may be modified to include a balloon 112 at distal end 82 of side member 68. Disposed over balloon 112 is a branch vessel stent 114. In this way, following partial or full deployment of main vessel stent 86 in a manner similar to that previously described, balloon 112 may be inflated to deploy branch vessel stent 114 into branch vessel BV. Following deployment of both main vessel stent 86 and branch vessel stent 114, catheter 64 may be withdrawn from the patient, leaving the two stents in place. Hence, by modifying catheter 64 as illustrated in FIG. 17, catheter 64 may be used to align and deploy main vessel stent 86 in a manner similar to that previously described as well as to deploy a branch vessel stent.

Figure 18:
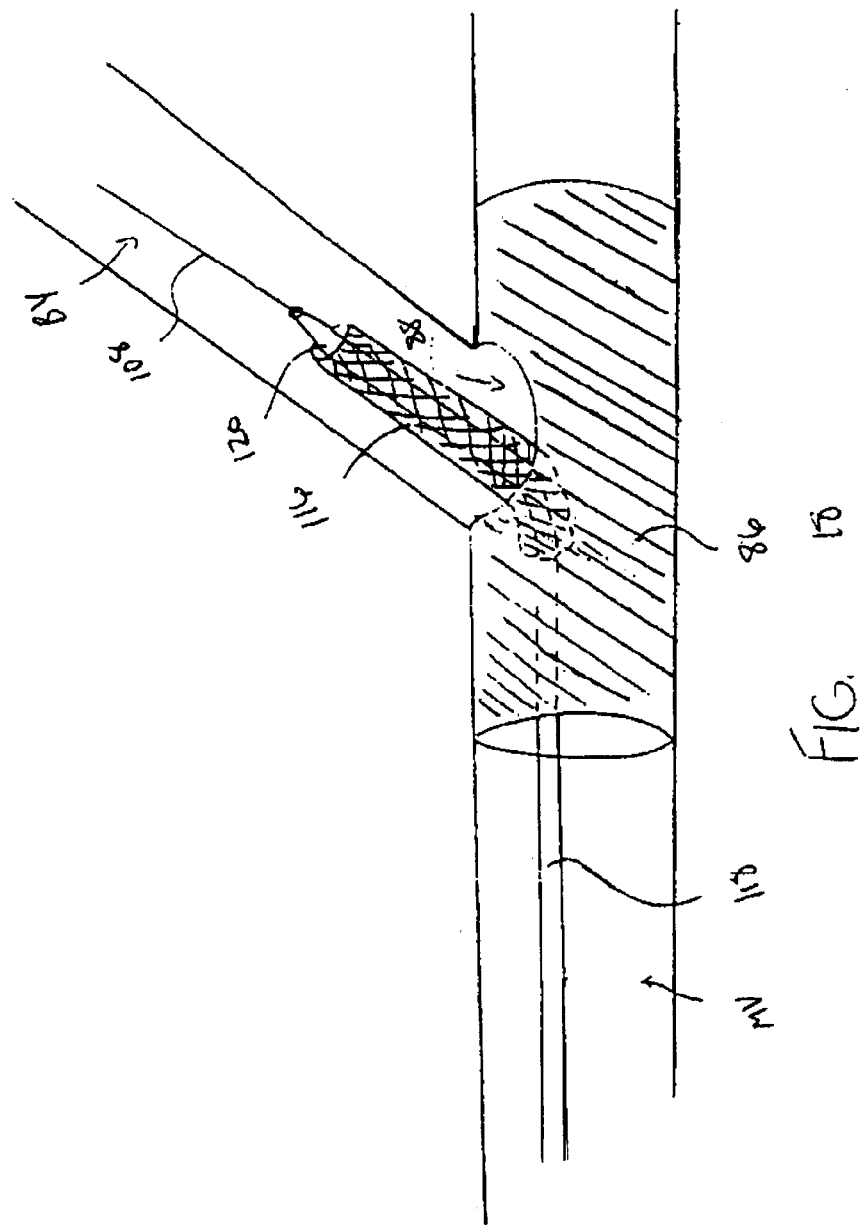
FIG. 18 illustrates a technique for deploying a branch vessel stent over a branch vessel guidewire following deployment of a main vessel stent according to the invention.
Figure 19:
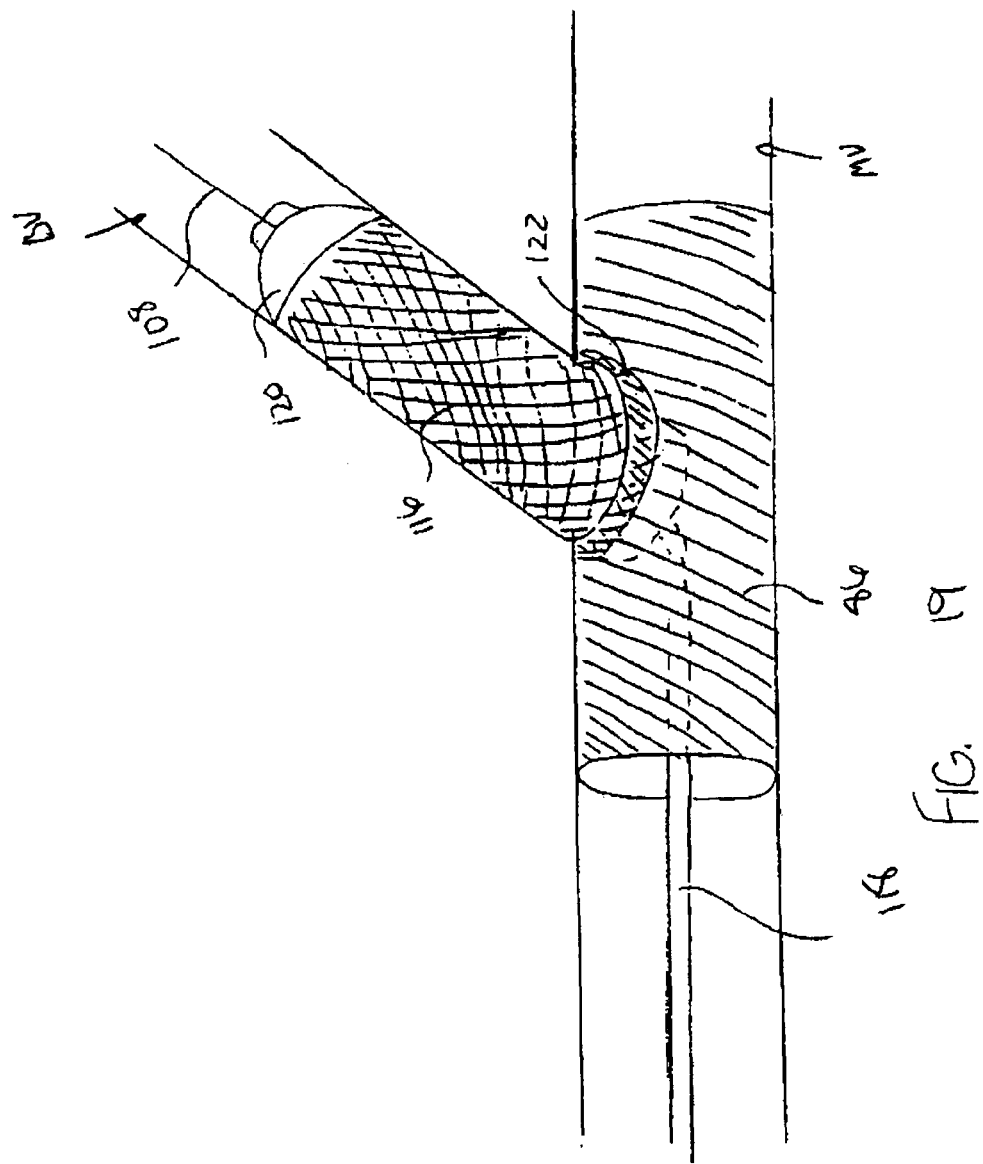
FIG. 19 illustrates inflation of a balloon on a balloon deployment device in order to deploy the branch vessel stent.

Another technique for introducing a branch vessel stent 116 into branch vessel BV following deployment of main vessel stent 86 using catheter 64 is illustrated in FIGS. 18 and 19. Following deployment of main vessel stent 86 in a manner similar to that previously described, catheter 64 is removed from the patient while leaving branch vessel guidewire 108 in place. A stent deployment device 118 having a balloon 120 is then advanced over guidewire 108 until branch vessel stent 116 (which is crimped about balloon 120) enters into branch vessel BV as illustrated in FIG. 18. Balloon 120 is then inflated as illustrated in FIG. 19 to deploy branch vessel stent 116. Balloon 120 may then be deflated and stent deployment device 118 withdrawn from the patient leaving in place main vessel stent 86 and branch vessel stent 116. Conveniently, branch vessel stent 116 may include a contacting portion 122 which remains disposed within side hole 88 to secure the proximal end of stent 116 to side hole 88 of main vessel stent 86. Such a contacting portion is described, for example, in PCT Patent Application No. PCT/US99/00835, filed Jan. 13, 1999, published under Publication Number WO99/36002 on Jul. 22, 1999, the complete disclosure of which is herein incorporated by reference.

Figure 20:
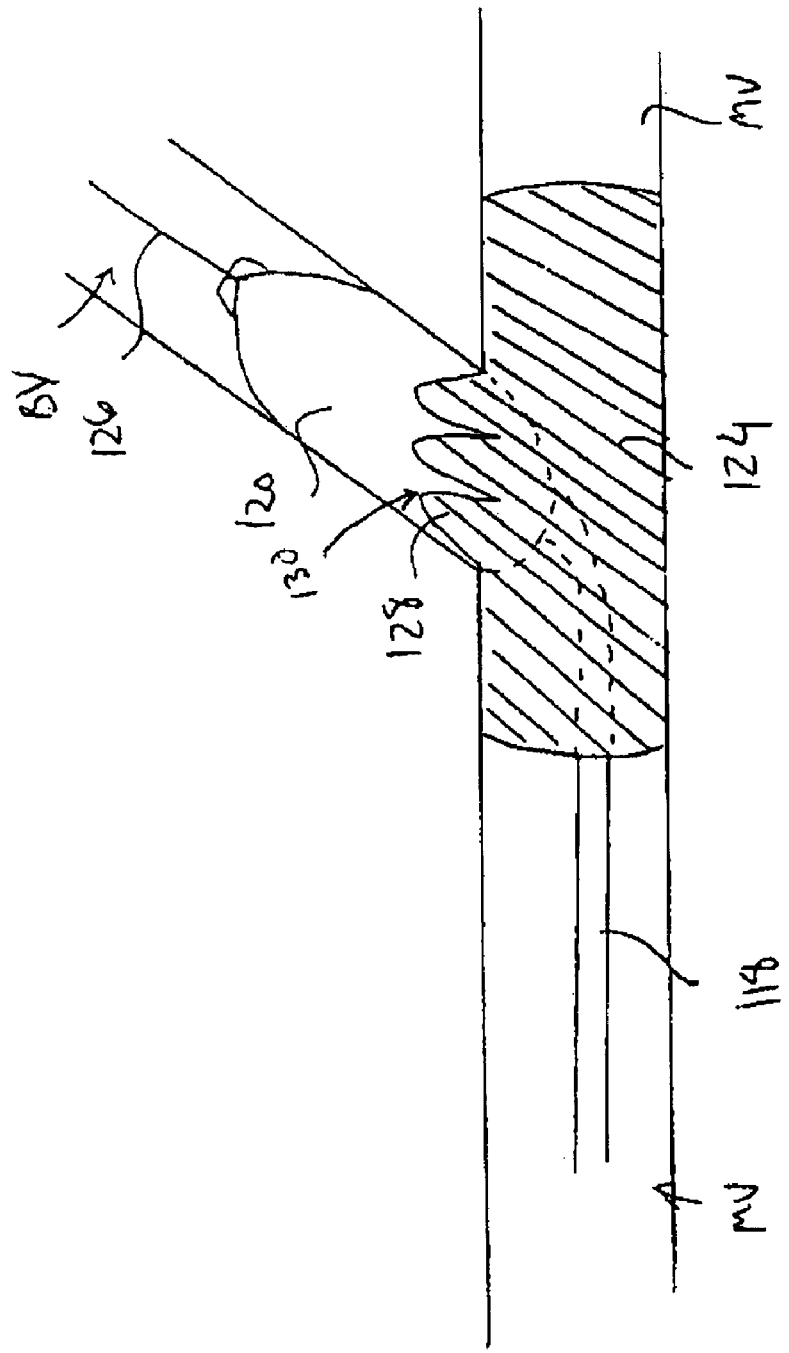
FIG. 20 illustrates an alternative embodiment of a main vessel stent having laterally deployable portions that may be deployed using the stent deployment device of FIGS. 7 and 18.

Shown in FIG. 20 is an alternative embodiment of a main vessel stent 124 that has been deployed in a main vessel MV. Conveniently, main vessel stent 124 may be deployed using any of the catheters described herein. After deployment of main vessel stent 124, the catheter is removed while a branch vessel guidewire 126 is kept in place within a branch vessel BV as shown in FIG. 20. Stent deployment device 118 of FIG. 19 may then be employed to deploy radially expandable portions 128 that extend laterally outward from the edges of a side hole 130. In this way, radially expandable portions 128 are pushed against the walls of branch vessel BV, with side hole 130 being positioned in registry with the ostium of branch vessel BV. Stents having radially expandable portions which extend laterally outward in such a manner are described in PCT Application No. WO 99/00835, previously incorporated herein by reference.

Figure 21:
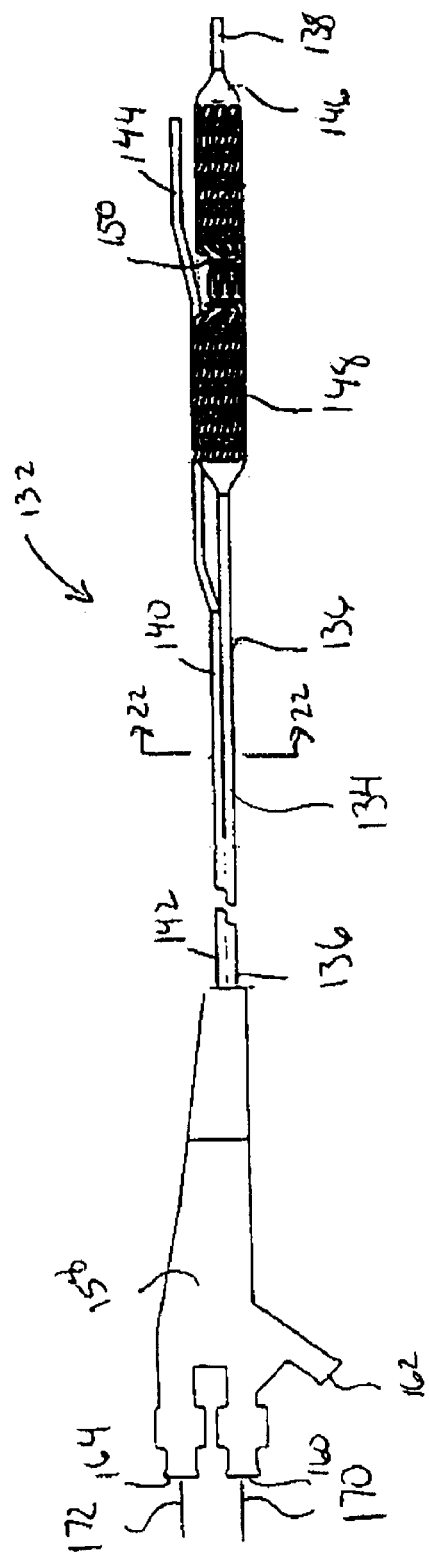
FIG. 21 illustrates another embodiment of a catheter for deploying a main vessel stent according to the invention.

Referring now to FIG. 21, an alternative embodiment of a stent delivery catheter 132 will be described. Catheter 132 comprises a catheter body 134 having a proximal end 136 and a distal end 138. Attached to catheter body 134 is a side member 140 having a proximal end 142 and a distal end 144. As shown in FIG. 21, distal end 144 of side member 140 is detached from distal end 138 of catheter body 134. The length of distal end 144 that is detached from catheter body 134 may be in the range from about 2 cm to about 10 cm. Such a configuration is advantageous in that it permits distal rotation of the device without rotating the main shaft from the proximal end. In this way, the clinician may easily align the side hole of the main stent with the ostium of the branch vessel without having to rotate the proximal end.

Disposed at distal end 138 is a balloon 146 over which a main vessel stent 148 having a side hole 150 is crimped. Distal end 144 of side member 140 passes between main vessel stent 150 and balloon 146 until exiting side hole 150. In this way, distal end 144 may be positioned within a branch vessel stent in a manner similar to that previously described with other embodiments.

Figure 22:
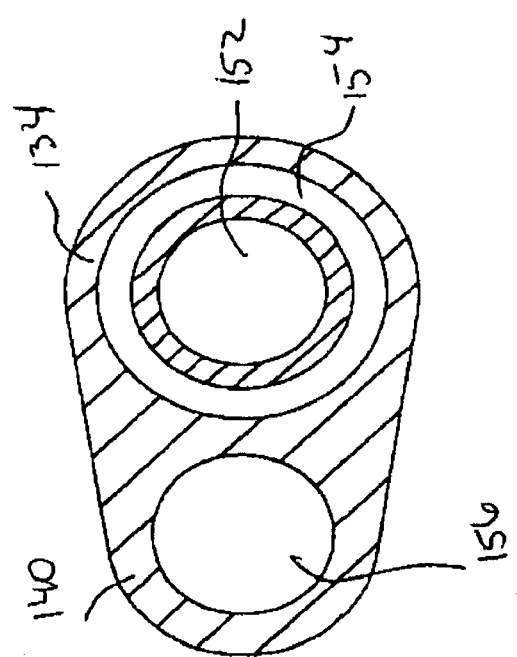
FIG. 22 is a cross sectional side view of the catheter of FIG. 21 taken along lines 22-22.

As shown in FIG. 22, passing through catheter body 134 is a main vessel guidewire lumen 152 and a balloon inflation lumen 154 that is disposed about main vessel guidewire lumen 152. Passing through side member 140 is a branch vessel guidewire lumen 156. In this way, catheter 132 may be tracked over main and branch vessel guidewires in a manner similar to that previously described with other embodiments. Further, balloon 146 may be inflated using balloon inflation lumen 154.

Figure 23:
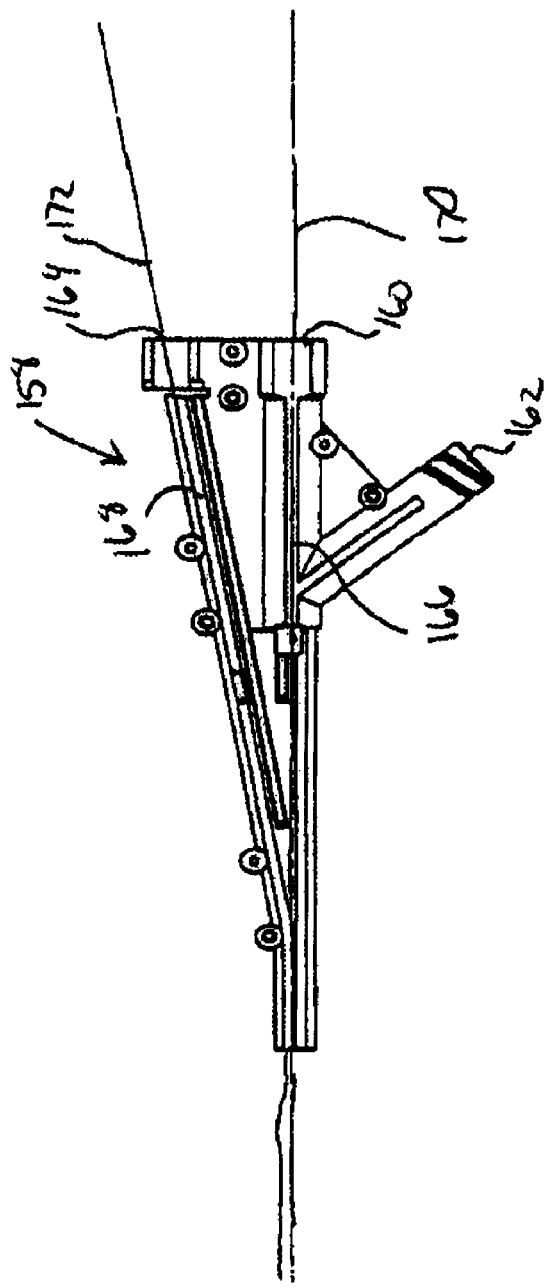
FIG. 23 is a cross sectional side view of a hub of the catheter of FIG. 21.

As best shown in FIGS. 21 and 23, a guidewire hub 158 is coupled to proximal ends 136 and 142. Guidewire hub 158 further includes a main vessel guidewire port 160, a balloon inflation port 162 and a branch vessel guidewire port 164. Balloon inflation port 162 is in fluid communication with balloon inflation lumen 154 (see FIG. 22) to permit balloon 146 to be inflated and deflated using an inflation device, such as a syringe, that is coupled to port 162. Main vessel guidewire port 160 leads to a main vessel guidewire channel 166, and branch vessel guidewire port 164 leads to a branch vessel guidewire channel 168. In this way, a main vessel guidewire 170 may be passed through port 160, through channel 166 and into guidewire lumen 152 (see FIG. 22). In a similar manner, a branch vessel guidewire 172 may be passed through port 164, through channel 168 and into lumen 156 (see FIG. 22).

Channels 166 and 168 are angled relative to each other, preferably at an angle in the range from about 0 to 20 degrees, and more preferably about 10 to about 20 degrees. By configuring channels 166 and 168 in this manner excessive friction may be avoided when positioning or moving the guidewires within catheter 132. In this way, catheter 132 may more easily be advanced over both guidewires 170 and 172 at the same time. Further, the guidewires are held sufficiently close to permit an operator to simultaneously grasp and hold onto both guidewires with one hand while withdrawing catheter 132 over the two guidewires with the other hand. In addition, the guidewires are held sufficiently far apart to permit a syringe to be coupled to ports 160 and 164, or to permit separate luer fittings to cover ports 160 and 164.

As shown in FIG. 24, catheter 132 may conveniently be included as part of a kit 200. Conveniently, kit 200 may also include instructions for use 202 which sets forth various procedures for deploying main vessel stent 148 using any of the techniques previously described. Instructions for use 202 may be in written or machine readable form. Further, it will be appreciated that kit 200 may alternatively include any of the other catheter embodiments described herein, and instructions 202 may describe any of the method set forth herein.

The invention has now been described in detail for purposes of clarity of understanding. However, it will be appreciated that certain changes and modifications may be practiced within the scope of the appended claims.

What is claimed is:

1. A catheter system for stent delivery to a vessel bifurcation, the vessel bifurcation having a main vessel and a branch vessel, comprising:

a catheter extending between a distal end and a proximal end, the catheter including a main vessel guidewire lumen that is adapted to receive a main vessel guidewire;

a stent being disposed over the catheter, the stent having a side hole through a wall thereof;

a first catheter radiopaque marker arranged on the catheter distal of the stent;

a second catheter radiopaque marker arranged on the catheter at a proximal end of the stent;

a third catheter radiopaque marker arranged on the catheter aligned with the side hole of the stent;

a side member disposed adjacent the catheter, the side member extending between a free distal end and a proximal end, the side member including a branch vessel guidewire lumen that is adapted to receive a branch vessel guidewire, the side member being fixedly attached to the catheter at a location proximal the stent, the free distal end of the side member arranged to extend through the side hole in the stent to a position distal of the side hole in the stent;

a first side member radiopaque marker positioned on the side member at the free distal end of the side member;

a second side member radiopaque marker positioned on the side member at a location spaced from the first side member radiopaque marker, wherein the second side member radiopaque marker is arranged to be aligned with the side hole of the stent when the free distal end of the side member extends into the branch vessel;

wherein the first catheter radiopaque marker and the first side member radiopaque marker are arranged side-by-side in a first configuration and the third catheter radiopaque marker and the second side member radiopaque marker are arranged side-by-side in a first configuration, wherein the first side member radiopaque marker and first catheter radiopaque marker are separated in a second configuration to indicate that the free distal end of the side member is advancing into the branch vessel.

2. The catheter system of claim 1, wherein the side member is flexible.

3. The catheter system of claim 1, further comprising a branch stent deployment device having a balloon, a guidewire lumen, an inflation lumen that is adapted to supply a fluid to inflate the balloon, and a branch vessel stent disposed over the balloon, wherein the branch stent deployment device is adapted to be advanced over the branch vessel guidewire.

4. The catheter system of claim 1, further comprising a balloon disposed at the distal end of the side member.

5. The catheter system of claim 1, wherein the distal end of the side member is tapered.

6. The catheter system of claim 1, wherein the distal end of the side member is fabricated from a fluoroscopically visible material.

7. The catheter system of claim 1, wherein the catheter and the side member are fabricated from pebax and graphite.

8. The catheter system of claim 1, further comprising a branch stent positioned on the side member.

9. The catheter system of claim 1, wherein the catheter further includes a balloon inflation lumen, and further comprising a proximal end hub having a main vessel guidewire channel that is coupled to the main vessel guidewire lumen, a branch vessel guidewire channel that is coupled to the branch vessel guidewire lumen, and a balloon inflation port that is coupled to the balloon inflation lumen.

10. The catheter system of claim 9, wherein the first and second guidewire channels are separated by about zero to 20°.

11. The catheter system of claim 1, wherein the distal end of the side member is unattached to the distal end of the catheter.

12. The catheter system of claim 11, wherein the length over which the distal end of the side member is unattached to the distal end of the catheter is approximately 2 to approximately 10 cm.

13. The catheter system of claim 1, wherein the side member is fixedly attached to the catheter at or near the proximal end of the catheter.

14. The catheter system of claim 13, wherein the side member is fixedly attached to the catheter along a length from the proximal end of the catheter to a location proximal to the stent.

15. The catheter system of claim 1, wherein the side member is fixedly attached to the catheter at a location that is spaced a distance from and is proximal to the stent.

16. The catheter system of claim 1, further comprising an expander disposed near the distal end of the catheter and wherein the stent is disposed over the expander such that upon expansion of the expander, the stent is configured to expand.

17. The catheter system of claim 16, wherein said expander is a balloon.

18. The catheter system of claim 1, wherein an outer diameter of the catheter is different than an outer diameter of the side member.

19. The catheter system claim 1, wherein the side member has a circular cross-section.

20. A catheter system for stent delivery to a vessel bifurcation, the vessel bifurcation having a main vessel and a branch vessel, comprising:
a catheter having a distal end, a proximal end, and a main vessel guidewire lumen that is adapted to receive a main vessel guidewire;
a stent having a side hole through a wall thereof, the stent being disposed over the catheter, wherein the stent hole is substantially alignable with a branch vessel when the stent hole is disposed substantially in the main vessel prior to expansion;
a first catheter radiopaque marker arranged on the catheter distal of the stent;
a second catheter radiopaque marker arranged on the catheter at a proximal end of the stent;
a third catheter radiopaque marker arranged on the catheter aligned with the side hole of the stent;
a side member disposed adjacent the catheter, the side member having a distal end, a proximal end, and a branch vessel guidewire lumen that is adapted to receive a branch vessel guidewire, the side member being integral with the catheter at a location proximal the stent wherein the distal portion of the side member is disposed at least partially within a portion of the stent and at least partially extending through and distal of the side hole of the stent;
a first side member radiopaque marker positioned on the side member at the distal end of the side member;
a second side member radiopaque marker positioned on the side member at a location spaced from the first side member radiopaque marker, wherein the second side member radiopaque marker is aligned with the side hole of the stent when the distal end of the side member has passed through the side hole and into the branch vessel;
wherein said catheter radiopaque markers and said side member radiopaque markers are moveable from a first configuration to a second configuration, wherein in the first configuration the first catheter radiopaque marker and the first side member radiopaque marker are side-by-side, wherein in the second configuration at least one of the side member radiopaque markers is separated from at least one of the catheter radiopaque markers.

21. The catheter system of claim 20, wherein the side member is flexible.

22. The catheter system of claim 20, further comprising a branch stent deployment device having a balloon, a guidewire lumen, an inflation lumen that is adapted to supply a fluid to inflate the balloon, and a branch vessel stent disposed over the balloon, wherein the branch stent deployment device is adapted to be advanced over the branch vessel guidewire.

23. The catheter system of claim 20, further comprising a balloon disposed at the distal end of the side member.

24. The catheter system of claim 20, wherein the distal end of the side member is tapered.

25. The catheter system of claim 20, wherein the distal end of the side member is fabricated from a fluoroscopically visible material.

26. The catheter system of claim 20, wherein the catheter and the side member are fabricated from pebax and graphite.

27. The catheter system of claim 20, further comprising a branch stent positioned on the side member.

28. The catheter system of claim 20, further comprising an expander disposed near the distal end of the catheter and wherein the stent is disposed over the expander such that upon expansion of the expander, the stent is configured to expand.

29. The catheter system of claim 28, wherein said expander is a balloon.

30. The catheter system of claim 29, wherein the catheter further includes a balloon inflation lumen, and further comprising a proximal end hub having a main vessel guidewire channel that is coupled to the main vessel guidewire lumen, a branch vessel guidewire channel that is coupled to the branch vessel guidewire lumen, and a balloon inflation port that is coupled to the balloon inflation lumen.

31. The catheter system of claim 30, wherein the first and second guidewire channels are separated by about zero to 20°.

32. The catheter system of claim 20, wherein the distal end of the side member is unattached to the distal end of the catheter.

33. The catheter system of claim 32, wherein the length over which the distal end of the side member is unattached to the distal end of the catheter is approximately 2 to approximately 10 cm.

34. The catheter system of claim 20, wherein the side member is fixedly attached to at least one location on the catheter.

35. The catheter system of claim 34, wherein the at least one location is at or near the proximal end of the catheter.

36. The catheter system of claim 34, wherein the at least one location is along a length, from the proximal end of the catheter to a location proximal to the stent.

37. The catheter system of claim 34, wherein the at least one location is spaced a distance from and is proximal to the stent.

38. The catheter system of claim 20, further comprising a connector coupled to the catheter, wherein the side member extends through the connector so as to be slidably positionable with respect to the catheter.

39. The catheter system of claim 20, wherein an outer diameter of the catheter is different than an outer diameter of the side member.

40. A catheter system for stent delivery to a vessel bifurcation, the vessel bifurcation having a main vessel and a branch vessel, comprising:
- a catheter having a distal end, a proximal end, and a main vessel guidewire lumen that is adapted to receive a main vessel guidewire;
- a first stent having a side hole through a wall thereof, the first stent being disposed over the catheter;
- a first catheter radiopaque marker arranged on the catheter distal of the stent;
- a second catheter radiopaque marker arranged on the catheter at a proximal end of the stent;
- a third catheter radiopaque marker arranged on the catheter aligned with the side hole of the first stent;
- a side member disposed adjacent and fixedly attached to at least one location on the catheter proximal the stent, the side member having a distal end, a proximal end, a branch vessel guidewire lumen that is adapted to receive a branch vessel guidewire, and at least two side radiopaque markers positioned on the side member, a first of the side radiopaque markers being spaced from a second of the side radiopaque markers, wherein the first catheter radiopaque marker and at least one of the side member radiopaque markers are side-by-side in a first configuration and separated in a second configuration; and
- a branch stent deployment device having a balloon, a guidewire lumen, an inflation lumen that is adapted to supply a fluid to inflate the balloon, and a branch vessel stent disposed over the balloon, wherein the branch stent deployment device is adapted to be advanced over the branch vessel guidewire;

wherein a distal portion of the side member is disposed within at least a portion of the first stent and extends through the side hole of the first stent to a position distal of the side hole.

41. A catheter system for stent delivery to a vessel bifurcation, the vessel bifurcation having a main vessel and a branch vessel, comprising:
- a catheter having a distal end, a proximal end, a main vessel guidewire lumen that is adapted to receive a main vessel guidewire, and catheter radiopaque markers positioned thereon;
- a side member disposed adjacent the catheter, the side member having a distal end, a proximal end, a branch vessel guidewire lumen that is adapted to receive a branch vessel guidewire, and first and second side member radiopaque markers positioned thereon, the side member being integral the catheter at a location proximal of the catheter radiopaque markers;
- a stent having a side hole through a wall thereof being disposed over the catheter, wherein a first of the catheter radiopaque markers is arranged on the catheter distal of the stent, a second of the catheter radiopaque markers is arranged on the catheter at a proximal end of the stent, and a third of the catheter radiopaque markers is arranged on the catheter aligned with the side hole of the stent; and
- a branch stent deployment device having a balloon, a guidewire lumen, an inflation lumen that is adapted to supply a fluid to inflate the balloon and a branch vessel stent disposed over the balloon, wherein the branch stent deployment device is adapted to be advanced over the branch vessel guidewire;

wherein a distal portion of the side member extends through the side hole of the stent to a position distal of the side hole along the catheter, and wherein said first and third catheter radiopaque markers and said first and second side member radiopaque markers are juxtaposed in a first configuration and separated in a second configuration.

42. The catheter system of claim 40, wherein the side member is integral with the catheter at a location proximal of the first stent.

* * * * *

UNITED STATES PATENT AND TRADEMARK OFFICE
CERTIFICATE OF CORRECTION

| | | |
|---|---|---|
| PATENT NO. | : 7,771,462 B1 | Page 1 of 1 |
| APPLICATION NO. | : 09/663111 | |
| DATED | : August 10, 2010 | |
| INVENTOR(S) | : Charles J. Davidson et al. | |

It is certified that error appears in the above-identified patent and that said Letters Patent is hereby corrected as shown below:

Column 16
Line 31: after "integral" and before "the", insert -- with --.

Signed and Sealed this

First Day of February, 2011

David J. Kappos
*Director of the United States Patent and Trademark Office*